(12) United States Patent
Melton et al.

(10) Patent No.: US 6,686,198 B1
(45) Date of Patent: *Feb. 3, 2004

(54) METHOD OF INDUCING AND MAINTAINING NEURONAL CELLS

(75) Inventors: Douglas A. Melton, Lexington, MA (US); Ali Hemmati-Brivanlou, New York, NY (US)

(73) Assignee: President and Fellows of Harvard College, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 71 days.

(21) Appl. No.: 08/835,279

(22) Filed: Apr. 9, 1997

Related U.S. Application Data

(63) Continuation of application No. 08/403,007, filed on Mar. 9, 1995, now abandoned, which is a continuation-in-part of application No. 08/136,748, filed on Oct. 14, 1993, now abandoned.

(51) Int. Cl.[7] ................................................. C12N 5/00
(52) U.S. Cl. ........................ 435/377; 435/325; 435/375
(58) Field of Search .......................... 435/172.1, 172.3, 435/6, 7.1, 325, 320.1, 375, 377; 536/23.5, 24.5; 530/324, 350; 514/2, 12, 44

(56) References Cited

U.S. PATENT DOCUMENTS

| | | | |
|---|---|---|---|
| 5,041,538 A | 8/1991 | Ling et al. | .................... 530/395 |
| 5,166,065 A | 11/1992 | Williams et al. | .......... 435/240.1 |
| 5,182,375 A | 1/1993 | Ling et al. | ................... 536/23.5 |

FOREIGN PATENT DOCUMENTS

| | | |
|---|---|---|
| WO | WO 89/01945 | 3/1989 |

OTHER PUBLICATIONS

Reilly, K.M. et al., *Cell*, 86 (5):743–54, Sep. 1996.*
Asashima, M. et al., *Int. Rev. Oytol.*, 191:1–52, 1999.*
Hemmati–Brivanlou, A. et al., *Cell*, 77(2):273–81, 1994.*
Hashimoto, M. et al., *J. Biol. Chem.*, 267 (11): 7203–7206, 1992.*
Yamada, R. et al., *Biochem. Biophys. Res. Comm.*, 187(1): 79–85, 1992.*
Fukui, A. et al., *Development Biology*, 159 : 131–139 (1993).*
Melton, D. A, *Science*, 252 : 234–41, 1991.*
Hemmati–Brivanlou, A. et al., *Nature*, 359: 609–14, 1992.*
Sokol, S.Y. et al., *Developmental Biology*, 154 : 348–55, 1992.*
Gurdon, J.B., *Cell*, 68 : 185–199, 1992.*
Lemaire, P., *Nature*, 359 : 586–87, 1992.*
Mather, J. P., *Endocrinology*, 132(6): 2732–34, 1993.*

Chang et al., "A Xenopus type I activin receptor mediates mesodermal but not neutral specification during embryogenesis", Development 1997 pp. 827–837.*
Schuldiner et al., "Effects to eight growht factors on the differentiation of cells derived from human embryonic stem cells", PNAS Oct. 10.2000, pp. 11307–11312.*
Attisano, Liliana et al., (1992) *Cell*, vol. 66, pp. 97–108.
Dohrmann, Cord E. et al., (1993) *Developmental Biology*, vol. 157, pp. 474–483.
Esch, F.S. et al., (1987) *Molecular Endocrinology*, vol. 1, pp. 849–855.
Green, Jeremy B. A. et al., (1992) *Cell*, vol. 71, pp. 731–739.
Hemmati–Brivanlou, Ali and Douglas A. Melton, (1992) *Nature*, vol. 359, pp. 609–614.
Hillier, S. G. and F. Miró, (1993) *Annals New York Academy of Sciences*, vol. 687, pp. 29–38.
Klar, Avihu, (1992) *Cell*, vol. 69, pp. 95–110.
Kreidberg, Jordan A. et al., (1993) *Cell*, vol. 74, pp. 679–691.
Mather, Jennie P., (1993) *Endocrinology*, vol. 132, pp. 2732–2734.
Melton, D.A., (1991) *Science*, vol. 252, pp. 234–241.
Paralkar, Vishwas M. et al., (1992) *Journal of Cell Biology*, vol. 119, pp. 1721–1728.
Patthy, László and Károly Nikolics, (1993) *TINS*, vol. 16, pp. 76–81.
Rosenberg, Michael B. et al., (1988) *Science (Reports)*, vol. 242, pp. 1575–1577.
Schubert, D. et al., (1990) *Nature*, vol. 344, pp. 868–870.
Sokol, S. Y. and D. A. Melton, (1992) *Developmental Biology*, vol. 154, pp. 348–355.
Thomsen, Gerald H. and Douglas A. Melton, (1993) *Cell*, vol. 74, pp. 433–441.
Buse, Eberhard et al., (1993) *Anatomy and Embryology*, vol. 187, pp. 259–268.
Gage, Fred H. and Lisa J. Fisher, (1991) *Neuron*, vol. 6, pp. 1–12.
Gurdon, J.B., (1992) *Cell*, vol. 68, pp. 185–199.
Guthrie, Sarah, (1991) *TINS*, vol. 14, pp. 123–126.
Langille, Robert M. and Brian K. Hall, (1989) *Biology Review*, vol. 64, pp. 73–91.
Lemaire, Patrick, (1992) *Nature*, vol. 359, pp. 586–587.

(List continued on next page.)

*Primary Examiner*—Marianne P. Allen
(74) *Attorney, Agent, or Firm*—Ropes & Gray LLP

(57) ABSTRACT

The present invention makes available a method for inducing neuronal differentiation and preventing the death or degeneration of neuronal cells both in vitro and in vivo. The subject method stems from the unexpected finding that, contrary to traditional understanding of neural induction, the default fate of ectodermal tissue is neuronal rather than mesodermal and/or epidermal. In particular, it has been discovered that preventing or antagonizing a signaling pathway in a cell for a growth factor of the TGF-β family can result in neuronal differentiation of that cell.

21 Claims, No Drawings

OTHER PUBLICATIONS

McConnell, Susan K., (1991) *Annual Review of Neuroscience,* vol. 14, pp. 269–300.

McKay, Ronald D.G., (1989) *Cell,* vol. 58, pp. 815–821.

Noden, Drew M., (1993) *Journal of Neurobiology,* vol. 24, pp. 248–261.

Placzek, Marysia et al., (1990) *Science (Reports),* vol. 250, pp. 985–988.

Saint–Jeannet, Jean–Pierre et al., (1993) *Experimental Cell Research,* vol. 207, pp. 383–387.

Smith, William C. and Richard M. Harland, (1992) *Cell,* vol. 70, pp. 829–840.

Snyder, Evan Y. et al., (1992) *Cell,* vol. 68, pp. 33–51.

Stemple, Derek L. and David J. Anderson, (1992) *Cell,* vol. 71, pp. 973–985.

Tannahill, D. and D.A. Melton, (1989) *Development,* vol. 106, pp. 775–785.

Wolswijk, Guus and Mark Noble, (1989) *Development,* vol. 105, pp. 387–400.

Hashimoto, Makato et al., (1992) *The Journal of Biol. Chem.,* vol. 267, 11 pp. 7203–7206.

Hashimoto, Makato et al., (1990) *Biochem. and Biophys. Research Comm.,* vol. 173, 1 pp. 193–200.

Hemmati–Brivanlou, Ali, and Douglas A. Melton (1994) *Cell* vol. 77, pp. 273–281.

Hemmati–Brivanlou, Ali, and Douglas A. Melton (1994) *Cell* vol. 77, pp. 283–295.

* cited by examiner-

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1178 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: CDS
      (B) LOCATION: 108..1067

(xi) SEQUENCE DESCRIPTION: SEQ ID NO: 1:

```
GCGGCCGCCC CCCCCCCGT CATTCAATAG AGTCCGGACT TGTGCCTGGT CCATTATCCC        60

ATCTCTCTCC ACTTGAGACT CTGCTCGTCC CACTCCCAGC ACTGAGG ATG TTA AAT       116
                                                  Met Leu Asn
                                                    1

GAA AGG ATC CAG CCG GGC ATG ATT TTC CTC CTG ACT GTC TCC CTG TGC       164
Glu Arg Ile Gln Pro Gly Met Ile Phe Leu Leu Thr Val Ser Leu Cys
      5                  10                  15

CAT TTC ATG GAA TAT CGC GCA GTC CAA GCT GGG AAT TGC TGG CTG CAG       212
His Phe Met Glu Tyr Arg Ala Val Gln Ala Gly Asn Cys Trp Leu Gln
 20                  25                  30                  35

CAG TCG AAG AAT GGC CGA TGT CAG GTT CTG TAC AGG ACA GAA CTG AGC       260
Gln Ser Lys Asn Gly Arg Cys Gln Val Leu Tyr Arg Thr Glu Leu Ser
                  40                  45                  50

AAA GAG GAA TGC TGC AAG ACT GGC AGA CTG GGC ACC TCA TGG ACA GAA       308
Lys Glu Glu Cys Cys Lys Thr Gly Arg Leu Gly Thr Ser Trp Thr Glu
              55                  60                  65

GAA GAT GTA CCC AAC AGC ACC CTC TTC AAA TGG ATG ATA TTT CAT GGA       356
Glu Asp Val Pro Asn Ser Thr Leu Phe Lys Trp Met Ile Phe His Gly
              70                  75                  80

GGG GCC CCA CAT TGC ATC CCC TGC AAA GAA ACA TGT GAG AAC GTA GAC       404
Gly Ala Pro His Cys Ile Pro Cys Lys Glu Thr Cys Glu Asn Val Asp
```

```
               85                  90                      95
TGT GGC CCT GGG AAG AAA TGT AAA ATG AAC AAG AAG AAC AAG CCG AGG       452
Cys Gly Pro Gly Lys Lys Cys Lys Met Asn Lys Lys Asn Lys Pro Arg
100             105                 110                 115

TGT GTC TGC GCT CCG GAT TGT TCC AAC ATT ACT TGG AAA GGT TCA GTG       500
Cys Val Cys Ala Pro Asp Cys Ser Asn Ile Thr Trp Lys Gly Ser Val
                120                 125                 130

TGC GGA ATT GAT GGC AAA ACC TAT AAG GAT GAG TGC GCT TTG CTC AAA       548
Cys Gly Ile Asp Gly Lys Thr Tyr Lys Asp Glu Cys Ala Leu Leu Lys
                135                 140                 145

GCC AAA TGT AAA GGG GTC CCG GAG CTG GAT GTG CAG TAC CAA GGA AAA       596
Ala Lys Cys Lys Gly Val Pro Glu Leu Asp Val Gln Tyr Gln Gly Lys
            150                 155                 160

TGC AAA AAG ACT TGC AGG GAC GTG CTG TGT CCA GGG AGC TCC TCG TGT       644
Cys Lys Lys Thr Cys Arg Asp Val Leu Cys Pro Gly Ser Ser Ser Cys
165             170                 175

GTG GTG GAT CAG ACC AAT AAC GCC TAC TGT GTG ACA TGT AAT CGG ATT       692
Val Val Asp Gln Thr Asn Asn Ala Tyr Cys Val Thr Cys Asn Arg Ile
180             185                 190                 195

TGC CCG GAG CCT ACC TCC CCT GAC CAA TAT CTG TGT GGG AAT GAT GGA       740
Cys Pro Glu Pro Thr Ser Pro Asp Gln Tyr Leu Cys Gly Asn Asp Gly
                200                 205                 210

ATA ACC TAT GGA AGT GCG TGC CAC CTG AGG AAG GCT ACC TGC CTG CTG       788
Ile Thr Tyr Gly Ser Ala Cys His Leu Arg Lys Ala Thr Cys Leu Leu
            215                 220                 225

GGC AGA TCC ATT GGA TTA GCC TAC GAG GGG AAA TGC ATA AAA GCC AAG       836
Gly Arg Ser Ile Gly Leu Ala Tyr Glu Gly Lys Cys Ile Lys Ala Lys
        230                 235                 240

TCT TGT GAA GAT ATT CAG TGC AGC GCT GGA AAG AAA TGC CTG TGG GAC       884
Ser Cys Glu Asp Ile Gln Cys Ser Ala Gly Lys Lys Cys Leu Trp Asp
    245                 250                 255

AGT AGA GTG GGT AGA GGT CGC TGT GCG CTG TGC GAT GAT CTG TGC GGA       932
Ser Arg Val Gly Arg Gly Arg Cys Ala Leu Cys Asp Asp Leu Cys Gly
260                 265                 270                 275

GAG AGC AAG TCA GAC GAT ACA GTG TGC GCC AGC GAC AAC ACG ACT TAC       980
Glu Ser Lys Ser Asp Asp Thr Val Cys Ala Ser Asp Asn Thr Thr Tyr
                280                 285                 290

CCG AGC GAG TGC GCC ATG AAA CAG GCA GCC TGC TCC ACG GGG ATT CTT      1028
Pro Ser Glu Cys Ala Met Lys Gln Ala Ala Cys Ser Thr Gly Ile Leu
            295                 300                 305

TTG GAA GTG AAA CAC AGT GGA TCT TGC AAC TGT AAG TGAATTACCG           1074
Leu Glu Val Lys His Ser Gly Ser Cys Asn Cys Lys
            310                 315                 320

CAACGCAGAG TAAGATTTCT AAAGGCAACC CCTCGGTAAT GAAGACTTTA AAGCAGCAAA    1134

ATACTTTTTT TTTTTTTTTT TCCTTTTTTT CTAAGGGAAT TCAG                     1178

(2) INFORMATION FOR SEQ ID NO: 2:

(i) SEQUENCE CHARACTERISTICS:
        (A) LENGTH: 319 amino acids
        (B) TYPE: amino acid
        (D) TOPOLOGY: linear (ii) MOLECULE TYPE: protein (xi) SEQUENCE DESCRIPTION: SEQ ID NO: 2:

Met Leu Asn Glu Arg Ile Gln Pro Gly Met Ile Phe Leu Leu Thr Val
 1               5                  10                  15

Ser Leu Cys His Phe Met Glu Tyr Arg Ala Val Gln Ala Gly Asn Cys
                20                  25                  30
```

-continued

```
Trp Leu Gln Gln Ser Lys Asn Gly Arg Cys Gln Val Leu Tyr Arg Thr
        35                  40                  45

Glu Leu Ser Lys Glu Glu Cys Cys Lys Thr Gly Arg Leu Gly Thr Ser
        50                  55                  60

Trp Thr Glu Glu Asp Val Pro Asn Ser Thr Leu Phe Lys Trp Met Ile
65                      70                  75                  80

Phe His Gly Gly Ala Pro His Cys Ile Pro Cys Lys Glu Thr Cys Glu
                    85                  90                  95

Asn Val Asp Cys Gly Pro Gly Lys Lys Cys Lys Met Asn Lys Lys Asn
                100                 105                 110

Lys Pro Arg Cys Val Cys Ala Pro Asp Cys Ser Asn Ile Thr Trp Lys
            115                 120                 125

Gly Ser Val Cys Gly Ile Asp Gly Lys Thr Tyr Lys Asp Glu Cys Ala
    130                 135                 140

Leu Leu Lys Ala Lys Cys Lys Gly Val Pro Glu Leu Asp Val Gln Tyr
145                 150                 155                 160

Gln Gly Lys Cys Lys Lys Thr Cys Arg Asp Val Leu Cys Pro Gly Ser
                165                 170                 175

Ser Ser Cys Val Val Asp Gln Thr Asn Asn Ala Tyr Cys Val Thr Cys
            180                 185                 190

Asn Arg Ile Cys Pro Glu Pro Thr Ser Pro Asp Gln Tyr Leu Cys Gly
        195                 200                 205

Asn Asp Gly Ile Thr Tyr Gly Ser Ala Cys His Leu Arg Lys Ala Thr
        210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Ser Ala Gly Lys Lys Cys
                245                 250                 255

Leu Trp Asp Ser Arg Val Gly Arg Gly Arg Cys Ala Leu Cys Asp Asp
            260                 265                 270

Leu Cys Gly Glu Ser Lys Ser Asp Asp Thr Val Cys Ala Ser Asp Asn
        275                 280                 285

Thr Thr Tyr Pro Ser Glu Cys Ala Met Lys Gln Ala Ala Cys Ser Thr
        290                 295                 300

Gly Ile Leu Leu Glu Val Lys His Ser Gly Ser Cys Asn Cys Lys
305                 310                 315
```

METHOD OF INDUCING AND MAINTAINING NEURONAL CELLS

REFERENCE TO RELATED APPLICATIONS

This application is a continuation of U.S. Ser. No. 08/403,007, filed Mar. 9, 1995, now abandonded, which is a continuation-in-part of U.S. Ser. No. 08/136,748, filed Oct. 14, 1993 now abandonded, and entitled "Method of Inducing and Maintaining Neuronal Cells". The disclosure of U.S. Ser. No. 08/136,748 is incorporated by reference.

GOVERNMENT FUNDING

Work described herein was supported in part by funding from the National Institutes of Health grant No. GM 44653. The United States Government has certain rights in the invention.

BACKGROUND OF THE INVENTION

Understanding the processes that lead from a fertilized egg to the formation of germ layers and subsequently to a body plan is a central goal of embryology. Much of what is known about the development of a vertebrate body plan comes from studies of amphibia where, at the tadpole stage, the main body axis consists of the dorsal structures notochord, spinal cord and somites organized anterior to posterior as head, trunk and tail. All animal tissues derive from the three germ layers and the mesoderm plays a pivotal role in organizing the body axis (Keller, R. in *Methods in Cell Biology*, eds Kay and Peng, Academic Press: San Diego, 1991). Mesodermal cells lead the movements of gastrulation (Keller et al. (1988) *Development* 103:193–210; and Wilson et al. (1989) *Development* 105:155–166), are required for the patterning of the nervous system (Mangold et al. (1933) *Natyrwissenschaften* 21:761–766; and Hemmati-Brivanlou et al. (1990) *Science* 250:800–802), and themselves give rise to the muscular, skeletal, circulatory and excretory systems. Moreover, a portion of the dorsal mesoderm from early gastrula, the Spemann organizer, can induce and organize a second body axis following transplantation to another site (Spemann et al. (1924) *Arch mikr Anat EntwMech* 100:599–638).

The origin of the nervous system in all vertebrates can be traced to the end of gastrulation. At this time, the ectoderm in the dorsal side of the embryo changes its fate from epidermal to neural. The newly formed neuroectoderm thickens to form a flattened structure called the neural plate which is characterized, in some vertebrates, by a central groove (neural groove) and thickened lateral edges (neural folds). At its early stages of differentiation, the neural plate already exhibits signs of regional differentiation along its anterior posterior (A-P) and mediolateral axis (M-L). The neural folds eventually fuse at the dorsal midline to form the neural tube which will differentiate into brain at its anterior end and spinal cord at its posterior end. Closure of the neural tube creates dorsal/ventral differences by virtue of previous mediolateral differentiation. Thus, at the end of neurulation, the neural tube has a clear anterior-posterior (A-P), dorsal ventral (D-V) and mediolateral (M-L) polarities (see, for example, *Principles in Neural Science* (3rd), eds. Kandel, Schwartz and Jessell, Elsevier Science Publishing Company: NY, 1991; and *Developmental Biology* (3rd), ed. S. F. Gilbert, Sinauer Associates: Sunderland Mass., 1991).

Before gastrulation the three germ layers are simply arranged, top to bottom, in a frog blastula. Ectoderm arises from the top, or animal pole; mesoderm from the middle, or marginal zone, and endoderm from the bottom or vegetal pole. Mesoderm can be induced in animal pole cells (animal caps) by signals emanating from the vegetal pole. Several peptide growth factors have been identified that can induce mesoderm in animal caps in vitro. When animal cap tissue is explanted from a blastula embryo and cultured in isolation it develops into a ball of epidermis. But in the presence of a mesoderm inducing factor, the animal cap will differentiate into mesodermal derivatives, including notochord, muscle and blood. Members of the fibroblast growth factor family, in particular basic fibroblast growth factor (bFGF), and the transforming growth factor-β (TGF-β) family, notably activins and Vg-1, are potent inducers in this assay. Xenopus homologues of the Wnt gene family may also have a role in mesoderm induction. Both Xwnt1 (McMahon et al. (1989) *Cell* 58, 1075–1084) and Xwnt8 messenger RNAs elicit dorsal mesoderm formation when injected into the ventral side of an early embryo, an activity shared by Vg-1, and to a lesser extent by activin RNA. bFGF and activin protein can be detected in the early embryo and although there are no data on the localization of activin, there is evidence that bFGF is present in the marginal zone and vegetal pole of early blastula. Vg-1 is present at the appropriate time and in the right region known to be responsible for mesoderm induction in vivo. Although Xwnt1 and Xwnt8 are not present at the proper time or place to effect dorsal mesoderm induction, there may be other Xwnts that fulfill this role.

Many types of communication take place among animal cells. These vary from long-range effects, such as those of rather stable hormones circulating in the blood and acting on any cells in the body that possess the appropriate receptors, however distant they are, to the fleeting effects of very unstable neurotransmitters operating over distances of only a few microns. Of particular importance in development is the class of cell interactions called embryonic induction; this includes influences operating between adjacent cells or in some cases over greater than 10 cell diameters (Saxen et al. (1989) *Int J Dev Biol* 33:21–48; and Gurdon et al. (1987) *Development* 99:285–306). Embryonic induction is defined as in interaction between one (inducing) and another (responding) tissue or cell, as a result of which the responding cells undergo a change in the direction of differentiation. This interaction is often considered one of the most important mechanism in vertebrate development leading to differences between cells and to the organization of cells into tissues and organs. Adult organs in vertebrates, and probably in invertebrates, are formed through an interaction between epithelial and mesenchymal cells, that is, between ectoderm/endoderm and mesoderm, respectively.

The effects of developmental cell interactions are varied. Typically, responding cells are diverted from one route of cell differentiation to another, by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185–199).

While there has been considerable progress in identifying molecules responsible for mesoderm induction, practically nothing is known about the molecular nature of neural induction. Candidate neural patterners are growth factors that are involved in mesoderm patterning in earlier stages and become localized later in a subset of cells in the nervous system. These molecules include different members of the Wnt, TGF-β and FGF families. Three members of the Wnt family Wnt-1, Wnt-3 and Wnt-3A, are localized in the roof plate (dorsal spinal cord) and a subset of brain cells. Good evidence that Wnt products pattern the neural tube comes from homozygote mice lacking the Wnt-1 gene product; these mutant mice display a strong abnormality in the anterior hindbrain and posterior midbrain (a region that coincides with engrailed-2 expressing cells)(McMahon et al. (1992) *Cell.* 69:581–595). Vg-1, BMP-4 (Jones et al. (1991) *Development.* 111:532–542) and dorsalin-1 (Blumberg et al. (1991) *Science* 253:194–196) are examples or TGF-β family members that display restricted expression in the embryonic nervous system (see also, Lyons et al. (1991) *Trends Genet* 7:408–412; and Massague et al. (1990) *J Biol Chem* 265:21393–21396). Dorsalin-1 inhibits the differentiation of motor neurons and induces migration of neural crest cells and thus may be involved in dorsal ventral patterning of the neural tube (Blumberg et al. (1991) *Science* 253:194–196). Finally acidic FGF (aFGF), basic FGF (bFGF) as well as the newly characterized FGF from Xenopus embryos, XeFGF, (Isaacs et al. (1992) *Development.* 114:711–20) are all expressed in some cells of the developing neural tube (Weise et al. (1992) *Cell & Tissue Research.* 276:125–130; and Tannahill et al. (1992) *Development.* 115:695–702).

Since the natural embryonic neural inducer or patterner has yet to be characterized, the analysis of the mechanisms of induction and patterning is difficult. However, studies have demonstrated that notochord can induce and pattern neural structures (Jones et al. (1989) *Development.* 107:785–791; and Sharpe et al. (1987) *Cell.* 50:749–758) which implies that the signals can travel vertically from the axial mesoderm to the overlying ectoderm. The finding that neuralization can be induced by mesoderm suggests that neural induction involves a signal acting in a paracrine fashion, the transduction of which appears to involve protein kinase C (Otte et al. (1991) *Science.* 251:570–573). A recent series of experiments, exploring one of Spemann's original ideas, have demonstrated that signals involved in both induction and patterning of the nervous system can also travel through the plane of the ectoderm (Dixon et al. (1989) *Development* 106:749–757; Doniach et al. (1992) *Science* 257:542–545; and Ruiz i Altaba, A. (1992) *Development.* 115:67–80). It is now accepted that both types of mechanisms coexist in the embryo and play a role in neurogenesis.

SUMMARY OF THE INVENTION

The present invention makes available a method for inducing neuronal differentiation and preventing the death and/or degeneration of neuronal cells both in vitro and in vivo. The subject method stems from the unexpected finding that, contrary to traditional understanding of neural induction, the default fate of ectodermal tissue is neuronal rather than mesodermal and/or epidermal. In particular, it has been discovered that preventing or antagonizing a signaling pathway in a cell for a growth factor of the TGF-β family (hereinafter "TGF-β-type growth factor"), can result in neuronal differentiation of that cell. In the subject method, signaling by the TGF-β-type growth factor is disrupted by antagonizing the inhibitory activity of the TGF-β-type growth factor. For instance, this can be accomplished by sequestering the growth factor with a growth factor binding protein (such as an activin-binding protein where the neural-inhibitory growth factor is activin) or by treating with an antagonist which competes with the growth factor for binding to a growth factor receptor on the surface of the cell of interest.

In one embodiment of the subject method, inducing cells to differentiate to a neuronal cell phenotype comprises contacting the cells with an agent which antagonizes the biological action of at least one polypeptide growth factor of the TGF-β family which normally induces the cells to differentiate to a non-neuronal phenotype. The antagonizing agent can inhibit the biological activity of the TGF-β-type growth factor, for example, by preventing the growth factor from binding its receptors on the surface of the treated cells. In another embodiment, the antagonizing agent binds to the growth factor and sequesters the growth factor such that it cannot bind its receptors.

To further illustrate the invention, the antagonizing agent can be selected from a group consisting of a follistatin, an α2-macroglobulin, a protein containing at least one follistatin module, and a truncated receptor for a growth factor of the TGF-β family. In the instance of the truncated receptor, it can be a soluble growth factor-binding domain of a TGF-β receptor, or, in another embodiment, the truncated receptor can be a membrane bound receptor and comprises an extracellular growth factor-binding domain of a TGF-β receptor, a transmembrane domain for anchoring the extracellular domain to a cell surface membrane, and a dysfunctional cytoplasmic domain. In the latter embodiment, the truncated receptor is recombinantly expressed in the treated cell.

In certain embodiments of the present method, the TGF-β-type growth factor which inhibits neuronal differentiation is an activin. In such instances, the method comprises contacting the cells with an agent which disrupts the activin signaling pathway in the cells, causing the cells to default to neuronal differentiation, rather than, for instance, mesodermal and/or epidermal fates.

The present method can be used in vitro, for example, to induce cells in culture to differentiate to a neuronal phenotype. Moreover, the present method is amenable to therapeutic application, and as described below, can be used to treat neurodegenerative disorders associated with, for example, the progressive and persistent loss of neuronal cells, such as which occurs with Alzheimer's disease, Parkinson's disease, amyotrophic lateral sclerosis, Pick's disease, Huntington's disease, multiple sclerosis, neuronal damage resulting from anoxia-ischemia, neuronal damage resulting from trauma, and neuronal degeneration associated with a natural aging process.

DETAILED DESCRIPTION OF THE INVENTION

As described herein, a collective group of experiments performed with either a truncated activin receptor conferring a dominant negative effect, or with a recombinant follistatin or inhibin, establish that a signaling pathway of a growth factor of the TGF-β family is involved in inhibiting neural induction in vivo. The present findings indicate, for the first time in vertebrates, that neuralization is a default state. As described in the Examples below, our results indicate that activin, or any other member of the TGF-β family that interacts with the truncated activin receptor, can inhibit neural induction, as these TGF-β signals instruct cells towards non-neuronal facts such as epidermal, mesodermal or endodermal fate. Inhibition of signal transduction by a TGF-β-type growth factor, by either the truncated activin receptor, follistatin, or inhibin, induced cells of the intact animal cap to switch to a neuronal fate in the absence of any detectable mesoderm. This data indicates that presumptive neural tissue in animal caps can respond to TGF-β-type growth factor and form mesodermal and/or epidermal tissues, but if this tissue specification by the factor is blocked, the cells become neural. As described below, activin is strongly implicated as the TGF-β-type growth factor that inhibits neuronal differentiation. Both activin and its receptor are present naturally in the animal cap, indicating that an endogenous activity that blocks activin signaling switches the tissue from an ectodermal to a neural fate. Thus, endogenous activin may act as a neural inhibitor (acting to induce epidermal development and/or mesoderm), and neuralization requires the inhibition of activin activity.

The present invention makes available a method for inducing neuronal differentiation and/or preventing the death or degeneration of neuronal cells. In general, the method comprises contacting a cell, either in vivo or in vitro, with an agent capable of antagonizing the biological action of a protein from the family of transforming growth factor-βs. The mechanism of action of the antagonist can, for example, comprise: competitive or non-competitive binding to a cell-surface receptor for the growth factor; sequestration of the growth factor; or inhibition of signal transduction events mediated by the growth factor receptor. Representative embodiments are described in more detail below.

The subject method stems from the unexpected finding that, contrary to traditional understanding of neural induction, the default fate of ectodermal tissue is neuronal rather than epidermal. In particular, it has been discovered that preventing or antagonizing a TGF-β-type growth factor signaling pathway for a cell can result in neuronal differentiation of that cell. In the subject method, signaling by the TGF-β-type growth factor is disrupted by antagonizing the inhibitory activity of the TGF-β-type growth factor. For instance, this can be accomplished by sequestering the growth factor with a growth factor binding protein (such as an activin-binding protein) or by treating with an antagonist which competes with the growth factor for binding to a growth factor receptor on the surface of the cell of interest.

As described herein, the present method can be used in vitro, for example, to induce cells in culture to differentiate to a neuronal phenotype. In one embodiment, the differentiated cells are subsequently continued in culture, and can be used to provide useful in vitro assay systems as well as valuable research tools for further understanding neural development. In another embodiment, the differentiated cells are used in vivo for transplantation. Moreover, the present method is amenable to therapeutic application, and as described below, can be used to treat neurodegenerative disorders associated with, for example, the progressive and persistent loss of neuronal cells, such as which occurs with Parkinson's disease, Alzheimer's disease, amyotrophic lateral sclerosis, and Huntington's disease.

While the following description, for clarity, describes the use of agents which antagonize activin signaling, it is understood that many such agents can also bind or otherwise antagonize other TGF-β-type growth factors and thereby disrupt their inhibition, if any, of neuralization. As used herein, the terms "transforming growth factor-beta" and "TGF-β" denote a family of structurally related paracrine polypeptides found ubiquitously in vertebrates, and prototypic of a large family of metazoan growth, differentiation, and morphogenesis factors (see, for review, Massaque et al. (1990) *Ann Rev Cell Biol* 6:597–641; and Sporn et al. (1992) *J Cell Biol* 119:1017–1021). Moreover, the present invention, namely the discovery that neuralization is a default state, will readily allow identification of other factors, including other TGF-β-like growth factors, which inhibit a cell from reaching this default (e.g. actively induce non-neuronal differentiation). In light of this understanding, agents which disrupt these factors are specifically contemplated by the present invention.

An agent capable of antagonizing the signaling pathway of a TGF-β factor involved in preventing neuronal differentiation, so as to cause a cell to default to neuronal differentiation, is herein referred to as a neuralizing agent, or "NA".

In one embodiment, the NA is an activin-binding protein which can reduce the bioavailability of activin, e.g. by sequestering activin in the extracellular milleu, with exemplary activin-binding agents including follistatins, α2-macroglobulin, and activin receptors. Other activin-binding proteins of the present method can include agrin, agrin-related proteins, and other proteins containing follistatin modules. In a preferred embodiment, the NA has a binding affinity for activin on the order of, or greater than, that of either a follistatin or an activin receptor.

In an illustrative embodiment of the present method, the NA is a follistatin able to bind and sequester activin. Follistatins are single chain, glycosylated polypeptides that were first isolated based on their ability to inhibit follicle-stimulating hormone release. Follistatins from several species, including human, have been structurally characterized and cloned. (See, for example, Esch et al. (1987) *Mol. Endocrinology* 11:849; Ling et al. International Publication No. WO 89/01945; Ling et al. U.S. Pat. No. 5,182,375; Ling et al. U.S. Pat. No. 5,041,538; and Inouye et al. (1991) *Endocrinology* 129:815–822). For instance, two forms of human follistatin have been cloned and expressed, one having 315 amino acid residues, and one having 288 amino acid residues. (Inouye et al., supra). Human follistatin is available through the National Hormone and Pituitary Program of the NIH. In a one embodiment, the follistatin of the present method is of the class of shorter follistatins (e.g. the 288 a.a. human homolog), since, as described below, these forms appear to have a greater binding affinity for activin, relative to the larger forms of follistatin.

In another exemplary embodiment, the activin-binding protein can be an activin receptor, or portion thereof. Activin receptors have also been cloned from several species. (Attisano et al. (1992) *Cell* 68:97–108; and Gerogi et al. (1990) *Cell* 61:635–645). In embodiments of the present invention in which it is desirable for the NA to be a diffusible molecule, a soluble extracellular portion of an activin receptor can be used, provided the extracellular portion is chosen so as to retain activin-binding. For example, a soluble form of an activin receptor can be generated using the cloned activin receptor gene of Attisano et al., which includes an endogenous signal sequence for secretion (Attisano et al. (1992) *Cell* 68:97–108). For instance, a stop codon can be introduced at a site 5' of the gene encoding the transmembrane domain (e.g. the ACC encoding Thr-134 can be mutated to TAA). Moreover, as described below, the truncated activin receptor can be engineered as fusion protein to include other polypeptide sequences.

In yet another illustrative embodiment of the present invention, the cell can be contacted with an activin antagonist which inhibits activin binding to its cognate receptor on the treated cell by competitively, or non-competitively, binding to the receptor protein. Such neuralizing agents can be utilized to block activin signaling and thereby induce the treated cell to undergo neuronal differentiation or to maintain its existing neuronal differentiation. A number of potential activin antagonists of this type are known in the art, including the family of inhibins. Inhibins and activins were first isolated and purified from follicular fluid on the basis of their ability to inhibit (inhibin) or stimulate (activin) FSH release by pituitary cells. Mature inhibin is typically a heterodimeric glycoprotein composed of a common α-subunit and one of two β subunits, $β_A$ and $β_B$. In addition to inhibins, the subject invention can be carried out using activins that have been mutagenized to create activin variants which act antagonistically to activin in neuronal induction. Activins are homodimeric forms of inhibin β-subunits (e.g. $β_Aβ_A$ or $β_Aβ_B$). Such antagonists can be generated, for example, by combinatorial mutagenesis techniques well known in the art (See, for example, Ladner et al. PCT publication WO 90/02909; Garrard et al., PCT publication WO 92/09690; Marks et al. (1992) J. Biol. Chem. 267:16007–16010; Griffths et al. (1993) EMBO J 12:725–734; Clackson et al. (1991) Nature 352:624–628; and Barbas et al. (1992) PNAS 89:4457–4461). Furthermore, peptidomimetics (e.g. of activin or inhibin) or other small molecules, such as may be identified in the assays set out below, can be used to antagonize activin signalling by binding to the receptor and precluding functional binding (or receptor oligomerization) by activin.

In still further embodiments, the neuralizing agent acts to block signal transduction by the activin receptor irrespective of activin binding. Such agents include dominant negative receptors which, unlike the soluble form of the receptor, are membrane bound, e.g. which include a transmembrane domain and at least a portion of a cytoplasmic domain. Such receptors, rather than merely sequestering activin from functional receptors, are incapable of activating appropriate intracellular second messenger pathways in response to activin binding. Expression of these dominant negative receptors in cells expressing wild-type receptor can render the cells substantially insensitive to activin, e.g. by formation of non-productive oligomers with the wild-type receptor. Likewise, other agents which inhibit the activin receptor second messenger pathways downstream of the activin receptor can be used to inhibit activin-mediated induction of cells.

Yet another embodiment of the subject assay features the use of an isolated nucleic acid construct for inhibiting synthesis of an activin receptor in the targeted cell by "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding an activin receptor so as to inhibit expression of that receptor, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes an activin receptor. Alternatively, the antisense construct can be an oligonucleotide probe which is generated ex vivo and which, when introduced into the treated cell causes inhibition of expression by hybridizing with the mRNA and/or genomic sequences of an activin receptor gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256, 775). Additionally, general approaches to constructing oligomers useful in antisense therapy have been reviewed, for example, by van der Krol et al. (1988) *Biotechniques* 6:958–976; and Stein et al. (1988) *Cancer Res* 48:2659–2668.

In certain embodiments, when appropriate, the neuralizing agent can be a chimeric protein comprising a moiety that binds a component of the extracellular matrix. Such a chimeric NA can be useful in circumstances wherein diffusion of the NA from a treatment site is undesirable, and will function to such an end by virtue of localizing the chimeric NA at or proximate a treatment site. An NA of this embodiment can be generated as the product of a fusion gene, or by chemical cross-linking. For instance, a number of proteins have been characterized from the extracellular matrix (ECM) of tissues that will support the localization of a chimeric NA at a target site. One example of a well characterized protein is fibronectin. Fibronectin is a large adhesive glycoprotein with multiple functional domains. Several of these domains have matrix attachment activity. For example, one of these is a single "type-III repeat" which contains a tetrapeptide sequence R-G-D-S (Pierschbacher et al. (1984) *Nature* 309:30–3; and Kornblihtt et al. (1985) *EMBO* 4:1755–9). Peptides as small as pentapeptides containing these amino acids are able to support attachment to a cell through binding ECM components (Ruoslahti et al. (1987) *Science* 238:491–497; Pierschbacher et al. (1987) *J. Biol. Chem.* 262:17294–8.; Hynes (1987) *Cell* 48:549–54; and Hynes (1992) *Cell* 69:11–25). In fact, several companies have commercialized products based on this cell attachment sequence for use as reagents in cell culture and various biomaterials applications. See for example recent catalogs from Telios Pharmaceutical, BRL, Stratagene, Protein Polymer Technologies etc., as well as U.S. Pat. Nos. 4,517,686; 4,589,881; 4,578,079; 4,614,517; 4,661,111; and 4,792,525. Accordingly, fibronectin binding sequences can be added, for example, to the soluble activin receptor described herein.

Another aspect of the present invention relates to a method of inducing and/or maintaining a differentiated state, and/or enhancing survival of a neural cell responsive to activin induction, by contacting the cell with a neuralizing agent (e.g. an activin antagonist). For instance, it is contemplated by the invention that, in light of the present finding of an apparently broad involvement of activin in the formation of ordered spatial arrangements of differentiated neural tissues in vertebrates, the subject method could be used to generate and/or maintain an array of different neural tissue both in vitro and in vivo. The neuralizing agent can be, as appropriate, any of the preparations described above, including isolated polypeptides, gene therapy constructs, antisense molecules, peptidomimetics or agents identified in the drug assays provided herein.

For example, the present method is applicable to cell culture technique. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). Once a neuronal cell has become terminally-differentiated it typically will not change to another terminally differentiated cell-type. However, neuronal cells can nevertheless readily lose their differentiated state. This is commonly observed when they are grown in culture from adult tissue, and when they form a blastema during regeneration. The present method provides a means for ensuring an adequately restrictive environment in order to maintain neuronal cells at various stages of differentiation, and can be employed, for instance, in cell cultures designed to test the specific activities of other trophic factors. In such embodiments of the subject method, the cultured cells can be contacted with a neuralizing agent of the present invention in order to induce neuronal differentiation (e.g. of a stem cell), or to maintain the integrity of a culture of terminally-differentiated neuronal cells by preventing loss of differentiation. The source of the neuralizing agent in the culture can be derived from, for example, a purified or semi-purified protein composition added directly to the cell culture media, or alternatively, released from a polymeric device which supports the growth of various neuronal cells and which has been doped with the neuralizing agent. If appropriate, the source of the neuralizing agent can also be a cell that is co-cultured with the intended neuronal cell and which produces a recombinant neuralizing agent. Alternatively, the source can be the neuronal cell itself which as been engineered to produce a recombinant neuralizing agent. In an exemplary embodiment, a naive neuronal cell (e.g. a stem cell) is treated with an activin antagonist in order to induce differentiation of the cells into, for example, sensory neurons or, alternatively, motorneurons. Such neuronal cultures can be used as convenient assay systems as well as sources of implantable cells for therapeutic treatments.

To further illustrate potential uses, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265–289; and Freund et al. (1985) *J Neurosci* 5:603–616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. Thus, use of activin antagonist for maintenance of neuronal cell cultures can help to provide a source of implantable neuronal tissue. The use of a neuralizing agent in the culture can be to prevent loss of differentiation, or where fetal tissue is used, especially neuronal stem cells, a neuralizing agent of the present invention can be used to induce differentiation.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of an activin-disrupting agent employed in the present method to culture such stem cells can be to induce differentiation of the uncommitted progenitor and thereby give rise to a committed progenitor cell, or to cause further restriction of the developmental fate of a committed progenitor cell towards becoming a terminally-differentiated neuronal cell. For example, the present method can be used in vitro to induce and/or maintain the differentiation of neural crest cells into glial cells, schwann cells, chromaffin cells, cholinergic sympathetic or parasympathetic neurons, as well as peptidergic and serotonergic neurons. The neuralizing agent can be used alone, or can be used in combination with other neurotrophic factors which act to more particularly enhance a particular differentiation fate of the neuronal progenitor cell. In the later instance, the neuralizing agent might be viewed as ensuring that the treated cell has achieved a particular phenotypic state such that the cell is poised along a certain developmental pathway so as to be properly induced upon contact with a secondary neurotrophic factor. In similar fashion, even relatively undifferentiated stem cells or primature neuroblasts can be maintained in culture and caused to differentiate by treatment with the subject neuralizing agents. Exemplary primative cell cultures comprise cells a harvested from the neural plate or neural tube of an embryo even before much overt differentiation has occurred.

The method of the present invention will also facilitate further determination of a potential role of follistatin as a "morphogen", that is, a molecule whose tight threshold of concentration determines specific cell fate during development (Wolpert, L. (1969) *J. Theor Biol.* 25:1–47). One of the first molecules to qualify as a morphogen was bicoid, a DNA binding protein whose graded distribution in the syncytium of the Drosophila embryo leads to the generation of specific cell fates (Driever et al. (1988) *Cell* 54:95–104). More recently two factors, activin in Xenopus embryos (Green et al. (1992) *Cell* 71:731–739) and decapentaplegic (dpl), (Ferguson et al. (1992) *Cell* 71:451–461)) in Drosophila embryos have been showed to act as morphogens in vitro. Both of these factors belong to the TGF-β superfamily of peptide growth factors and both can specify different cell fates at tight thresholds of concentration. Since follistatin is an inhibitor of activin and both activin ligand and receptor RNAs are expressed in the presumptive ectoderm, follistatin, like activin, may have morphogenic activity. Both the dominant negative activin receptor and follistatin, as described below, elicit neural tissue formation directly. Based on this data, it is asserted that neural tissue represents the default state vis-a-vis activin signaling in presumptive ectoderm. In this model, the amount of activin ligand and receptor present in the cap maintains the cells as epidermal, and additional activin changes the cells' fate to mesodermal. By inhibiting activin to varying degrees, follistatin could also act as a morphogen.

In an illustrative embodiment of an in vitro assay system, to test if follistatin (or another NA) can act as a morphogen, dissociated animal cap cells can be cultured and dosed with activin at a concentration sufficient to turn on a general mesodermal marker such as brachyury upon reassociation. The activity of activin can then be challenged with small incremental changes in follistatin protein concentration. Indicators that follistatin might serve as a morphogen will include the observation of small concentration differences giving rise to different cell fates, distinguishable by histology or through the use of cell-type specific molecular markers. These studies will allow for the determination of the extent of the number of independent cellular fates that exist in the presumptive ectoderm as well as, what proportion of animal cap cells become neural in response to different concentrations of follistatin.

Similar studies can be performed with stem cells, such as the neural crest cells described above, to determine if the concentration of follistatin (or other NA) is influential on the path of neuronal differentiation of uncommitted and committed progenitor cells, and ultimately whether concentration effects the particular terminally-differentiated derivation of the progenitor cells which arise.

In another embodiment, in vitro cell cultures can be used for the identification, isolation, and study of genes and gene products that are expressed in response to disruption of activin signaling, and therefore likely involved in neurogenesis. These genes would be "downstream" of the activin signal, and required for neuronal differentiation. For example, if new transcription is required for the neuralization, a subtractive cDNA library prepared with control animal caps and animal caps treated with follistatin can be used to isolate genes that are turned on or turned off by this process. The powerful subtractive library methodology incorporating PCR technology described by Wang and Brown is an example of a methodology useful in conjunction with the present invention to isolate such genes (Wang et al. (1991) *Proc.Natl.Acad.Sci. USA* 88:11505–11509). For example, this approach has been used successfully to isolate more than sixteen genes involved in tail resorption with and without thyroid hormone treatment in Xenopus. Utilizing control and treated caps, the induced pool can be subtracted from the uninduced pool to isolate genes that are turned on, and then the uninduced pool from the induced pool for genes that are turned off. From this screen, it is expected that two classes of mRNAs can be identified. Class I RNAs would include those RNAs expressed in untreated caps and reduced or eliminated in induced caps, that is the down-regulated population of RNAs. Class II RNAs include RNAs that are upregulated in response to induction and thus more abundant in treated than in untreated caps. RNA extracted from treated vs untreated caps can be used as a primary test for the classification of the clones isolated from the libraries. Clones of each class can be further characterized by sequencing and, their spatiotemporal distribution determined in the embryo by whole mount in situ and developmental northern blots analysis.

For example, in one embodiment of this subtractive assay, special attention can be given to genes that prove to be an immediate early response to neural induction. To qualify as such, these genes should fulfill the following four criteria. First, the RNA should appear quickly (10 to 30 minutes) following application of the inducer. To test this requirement, RNA can be isolated at different times from induced caps and scored for gene expression by northern blots. Second, the induction of the gene should not require previous protein synthesis. Thus, caps can be incubated with cycloheximide (5 $\mu$g/ml) prior to and during short incubation with follistatin (30 minutes) after which the caps can be allowed to remain in follistatin for longer periods of time (90 minutes) and then analyzed by northern blotting. This strategy has been used in a similar situation when Mix. 1, a homeobox gene exhibiting an immediate early response to both activin and bFGF was isolated from Xenopus animal caps (Rosa, F. M. (1989) *Cell.* 57:965–974). These conditions are sufficient to inhibit 75% to 80% of the protein synthesis during the period of induction and to abolish the induction of muscle actin mRNA in response to activin in late explants (Bolce et al. (1993) *Developmental Biology* 160). Third, immediate early response genes should be expressed as a result of contact with the inducer and not from a secondary cell-cell induction. One method to differentiate between these two responses is to dissociate the cells of the animal cap in Ca/Mg free medium, add follistatin and compare the amount of the induced transcript in dissociated cells versus intact caps. If the levels are comparable in both types of caps, then it may be concluded that cell-cell contact was not required for this induction and it is thus likely a direct response of follistatin treatment. Finally, these genes would be expected to be present and activated in the nervous system during neurogenesis.

Once isolated, the genes regulated by follistatin can be sequenced and their embryonic distribution can be determined by wholemount approaches. If their embryonic expression is in agreement with a possible neurogenic function, they can be tested for neuralizing activity in animal caps and in embryos as described herein for follistatin and other NAs.

Moreover, the present invention provides assays for identifying novel neuralizing agents. For example, an assay can comprise animal cap cells, or equivalent cells thereof, cultured in the presence of a TGF-$\beta$-type factor which inhibits neuralization such as activin. A portion of the cells are contacted with a candidate agent, and neuronal differentiation of any of the cells, is scored for by the presence of a neuronal marker, such as NCAM, being expressed by the cells.

Other embodiments of the assay can score simply for the ability of an added agent to inhibit protein-protein interaction between a TGF-$\beta$ and its cognate receptor. For instance, in one embodiment, the assay evaluates the ability of a compound to modulate binding between an activin polypeptide and an activin receptor. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with receptor proteins. Accordingly, in an exemplary screening assay of the present invention, the compound of interest is contacted with an activin receptor polypeptide which is ordinarily capable of binding an activin protein. To the mixture of the compound and receptor is then added a composition containing an activin polypeptide. Detection and quantification of receptor/activin complexes provides a means for determining the compound's efficacy at inhibiting complex formation between the receptor protein and the activin polypeptide. The efficacy of the compound can be assessed by generating dose response curves from data obtained using various concentrations of the test compound. Moreover, a control assay can also be performed to provide a baseline for comparison. In the control assay, isolated and purified activin polypeptide is added to a composition containing the receptor protein, and the formation of receptor/activin complex is quantitated in the absence of the test compound.

Complex formation between the activin polypeptide and an activin receptor may be detected by a variety of techniques. For instance, modulation of the formation of complexes can be quantitated using, for example, detectably labelled proteins such as radiolabelled, fluorescently labelled, or enzymatically labelled activin polypeptides, by immunoassay, or by chromatographic detection.

Accordingly, a wide range of agents can be tested, such as proteins and polypeptides, as well as peptidomimetics and other small molecules (including natural products). For instance, a drug screening assay described above can be used in the reduction of the activin of inhibin proteins to generate mimetics, e.g. peptide or non-peptide agents, which are able to disrupt binding of an activin polypeptide of the present invention with an activin receptor. By employing, for example, scanning mutagenesis to map the critical amino acid residues of the activin protein involved in binding the activin receptor, peptidomimetic compounds can be generated which mimic those residues in binding to the receptor and which consequently can inhibit binding of activin to its receptor, as may be detected in a screening assay as described herein. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71.

In addition to the implantation of cells cultured in the presence of an NA and other in vitro uses described above, yet another objective of the present invention concerns the therapeutic application of activin-disrupting agents to enhance survival of neurons and other neuronal cells in both the central nervous system and the peripheral nervous system. The ability of follistatin to regulate neuronal differentiation not only during development of the nervous system but also presumably in the adult state indicates that NAs can be reasonably expected to facilitate control of adult neurons with regard to maintenance, functional performance, and aging of normal cells; repair and regeneration processes in chemically or mechanically lesioned cells; and prevention of degeneration and death which result from loss of differentiation in certain pathological conditions. In light of this understanding, the present invention specifically contemplates applications of the subject method to the treatment of (prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; (iv) chronic immunological diseases of the nervous system or affecting the nervous system, including multiple sclerosis; and (v) degenerative diseases of the retina.

Many neurological disorders are associated with degeneration of discrete populations of neuronal elements and may be treated with a therapeutic regimen which includes a neuralizing agent of the present invention. For example, Alzheimer's disease is associated with deficits in several neurotransmitter systems, both those that project to the neocortex and those that reside with the cortex. For instance, the nucleus basalis in patients with Alzheimer's disease were observed to have a profound (75%) loss of neurons compared to age-matched controls. Although Alzheimer's disease is by far the most common form of dementia, several other disorders can produce dementia. Many are age-related, occurring in far greater incidence in older people than in younger. Several of there are degenerative diseases characterized by the death of neurons in various parts of the central nervous system, especially the cerebral cortex. However, some forms of dementia are associated with degeneration of the thalmus or the white matter underlying the cerebral cortex. Here, the cognitive dysfumction results from the isolation of cortical areas by the degeneration of efferents and afferents. Huntington's disease involves the degeneration of intrastraital and cortical cholinergic neurons and GABAergic neurons. Pick's disease is a severe neuronal degeneration in the neocortex of the frontal and anterior temporal lobes, sometimes accompanied by death of neurons in the striatum. Treatment of patients suffering from such degenerative conditions can include the application of neuralizing agent polypeptides, or agents which mimic their effects, in order to manipulate, for example, the de-differentiation and apoptosis of neurons which give rise to loss of neurons. In preferred embodiments, a source of a neuralizing agent is stereotactically provided within or proximate the area of degeneration.

In addition to degenerative-induced dementias, a pharmaceutical preparation of a neuralizing agent can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. The present method is amanable to the treatment of disorders of the cerebellum which result in hypotonia or ataxia, such as those lesions in the cerebellum which produce disorders in the limbs ipsilateral to the lesion. For instance, a preparation of a neuralizing agent of the present invention can be used to treat a restricted form of cerebellar cortical degeneration involving the anterior lobes (vermis and leg areas) such as is common in alcoholic patients.

In yet another embodiment, the subject method is used to treat amyotrophic lateral sclerosis. ALS is a name given to a complex of disorders that comprise upper and lower motor neurons. Patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of an activin antagonist can be used alone or in conjunction with other neurotrophic factors such as CNTF, BDNF, or NGF to prevent and/or reverse motor neuron degeneration in ALS patients.

The neuralizing agents of the present invention can also be used in the treatment of autonomic disorders of the peripheral nervous system, which include disorders affecting the innervation of smooth muscle endocrine tissue (such as glandular tissue). For instance, neuralizing agent compositions may be useful to treat tachycardia or atrial cardiac arrythmias which may arise from a degenerative condition of the nerves innervating the striated muscle of the heart.

In yet another embodiment, the subject neuralizing agents can be used in the treatment of neoplastic or hyperplastic transformations, involving neural tissue. For instance, an activin antagonist likely to be capable of inducing differentiation of transformed neuronal cells to become post-mitotic or possibly apoptotic. Inhibition of activin-mediated inductive events may also involve disruption of autocrine loops, such as PDGF autostimulatory loops, believed to be involved in the neoplastic transformation of several neuronal tumors. The subject method may, therefore, be of use in the treatment of, for example, malignant gliomas, medulloblastomas, neuroectodermal tumors, and ependymonas.

The NA, or a pharmaceutically acceptable salt thereof, may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient (s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the NA, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, the pharmaceutical formulation includes, although not exclusively, NA solutions or a freeze-dried powder of an NA (such as a follistatin) in association with one or more pharmaceutically acceptable vehicles or diluents, and contained in buffered media at a suitable pH and isosmotic with physiological fluids. For illustrative purposes only and without being limited by the same, possible composition of formulations which may be prepared in the form of solutions for the treatment of nervous system disorders with an NA are given in the della Valle U.S. Pat. No. 5,218,094. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of the NA in isotonic solutions of the desired volume and include, but not exclusively, the use of buffered saline solutions with phosphate or citrate at suitable concentrations so as to obtain at all times isotonic pharmaceutical preparations of the desired pH, for example, neutral pH.

Methods of introduction of the NA at the site of treatment include, but are not limited to, intradermal, intramuscular, intraperitoneal, intravenous, subcutaneous, oral, and intranasal. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

Methods of introduction may also be provided by rechargable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of an NA at a particular target site. Such embodiments of the present invention can be used for the delivery of an exogenously purified NA, which has been incorporated in the polymeric device, or for the delivery of an NA produced by a cell encapsulated in the polymeric device.

An essential feature of certain embodiments of the implant is the linear release of the NA, which can be achieved through the manipulation of the polmer composition and form. By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The such implants is generally known in the art. See, for example, *Concise Encyclopedia of Medical & Dental Materials*, ed. by David Williams (MIT Press: Cambridge, Mass., 1990); and the Sabel et al. U.S. Pat. No. 4,883,666. In another embodiment of an implant, a source of cells producing the NA, or a solution of hydrogel matrix containing purified NA, is encapsulated in implantable hollow fibers. Such fibers can be pre-spun and subsequently loaded with the NA source (Aebischer et al. U.S. Pat. No. 4,892,538; Aebischer et al. U.S. Pat. No. 5,106,627; Hoffman et al. (1990) *Expt. Neurobiol.* 110:39–44; Jaeger et al. (1990) *Prog. Brain Res.* 82:41–46; and Aebischer et al. (1991) *J. Biomech. Eng.* 113:178–183), or can be co-extruded with a polymer which acts to form a polymeric coat about the NA source (Lim U.S. Pat. No. 4,391,909; Sefton U.S. Pat. No. 4,353,888; Sugamori et al. (1989) *Trans. Am. Artif. Intern. Organs* 35:791–799; Sefton et al. (1987) *Biotehnol. Bioeng.* 29:1135–1143; and Aebischer et al. (1991) *Biomaterials* 12:50–55).

In yet another embodiment of the present invention, the neuralizing agent can be administered as part of a combinatorial therapy with other agents. For example, the combinatorial therapy can include an neuralizing agent such as follistatin with at least one trophic factor. Exemplary trophic factors include nerve growth factor, ciliary neurotrophic growth factor, schwannoma-derived growth factor, glial growth factor, strectal derived neuronotrophic factor, platelet-derived growth factor, and scatter factor (HGF-SF). Other neural inductive proteins, such as hedgehog-like proteins, noggin, and ligands of the Notch receptor, may also be used in conjunction with the subject neuralizing agent. Antimitogenic agents can also be used, as for example, when proliferation of surroundig glial cells or astrocytes is undesirable in the regeneration of nerve cells. Examples of such antimitotic agents include cytosine, arabinoside, 5-fluorouracil, hydrozyurea, and methotrexate.

Moreover, certain of the neuralizing agents, such as the dominant negative activin receptors (either soluble of membrane bound), may be ammenable to delivery by gene therapy. For instance, expression constructs of the subject dominant negative receptors may be administered in any biologically effective carrier, e.g. any formulation or composition capable of effectively delivering the dominant negative receptor gene to cells in vivo. Approaches include insertion of the mutant receptor gene in viral vectors including recombinant retroviruses, adenovirus, adeno-associated virus, and herpes simplex virus-1, or recombinant bacterial or eukaryotic plasmids. While viral vectors transfect cells directly, plasmid DNA can also be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of activin expression are also useful for in vitro transduction of cells, such as for use in the ex vivo tissue culture systems described above.

Exemplification

The fact that neuralization was closely linked to mesoderm induction has hampered most of the previous effort invested in the molecular characterization of neural inducers and patterners. Thus, attempts to isolate factors involved in neural induction and patterning have ended in the identification and characterization of mesoderm inducers and modifiers. The data described in the Examples below demonstrate that two activin antagonists, the dominant negative form of the activin receptor (Δ1XAR1) and follistatin both elicit direct neuralization in embryonic explants without a prerequirement for mesoderm induction. In addition, a full length cDNA for Xenopus follistatin has been isolated and its embryonic localization shown to be in perfect agreement with a role in neural development in vivo. The observation that antagonizing the activin signal results in neuralization suggests, for the first time, that neural induction in vertebrates represents a default state.

Additionally, as described in the Examples below, the truncated activin receptor does not block mesoderm induction by exogenous FGF in animal caps, and yet endogenous FGF does not induce mesoderm in a significant fraction of embryos injected with Δ1XAR1. Furthermore, when half the embryo is injected with Δ1XAR1, that half lacks Xbra expression in all embryos tested (n=25) even though FGF is a potent inducer of brachyury in the animal cap assay. These data indicates that endogenous FGF signaling is not sufficient to rescue brachyury expression or mesoderm induction in the marginal zone of embryos injected with Δ1XAR1. At the same time, it is clear from other experiments with a dominant negative FGF receptor that FGF plays an important role in axial patterning, particularly for posterior structures (Amaya et al. (1991) Cell. 66:257–270). Taken together, these findings raise the possibility that FGF signaling at the time of mesoderm induction requires a functional activin pathway.

The invention now being generally described, it will be more readily understood by reference to the following examples which are included merely for purposes of illustration of certain aspects and embodiments of the present invention, and are not intended to limit the invention.

EXAMPLE 1

Inhibition of Activin Signaling by a Truncated Activin Receptor Induces Neural Structures in vivo To demonstrate the assertion that neuralization represents a default state requiring the inhibition of endogenous activin molecules, the ability of a dominant negative activin receptor to induce neuralization ectopically in embryos was assigned. A truncated version of XAR1 was constructed to contain the entire extracellular and transmembrane domains but which lacks nearly all of the cytoplasmic domain, including the serine/threonine kinase. To construct Δ1XAR1, a fragment of DNA from XAR1 (Hemmati-Brivanlou et al. (1992) Dev Dyn 194:1–11) encoding the entire extracellular domain (including the signal sequence), the transmembrane domain and 10 amino acid residues of the cytoplasmic domain and entirely free of 5' and 3' untranslated sequences was subcloned into pSP64T (Kreig et al. (1984) Nuc Acid Res 12:7057–7070). The linearized plasmid was transcribed in vitro with SP6 to generated capped sense RNA. The resulting RNA encoding the truncated activin receptor was injected into cells of either wild type or ventralized embryos. In wild type embryos two types of experiments were performed. In the first set of experiments, RNA encoding Δ1XAR1 was injected in the animal pole of the early embryo (e.g. two cell stage). The animal pole is the region of the embryos that gives rise to the future ectoderm which in turn becomes epidermal or neural in fate. Targeting Δ1XAR1 to the site of prospective ectoderm leads to the generation of embryos with grossly exaggerated neural structures mostly of anterior character. For instance, embryos form up to eight eyes and five cement glands, and whole mount immunohistochemistry with an anti-NCAM antibody reveals that most of the cells of the embryo are positively stained with a general neural marker. Since the animal pole of the embryo participates in neurogenesis, this experiment demonstrates that neural induction has been amplified.

In the second set, a few cells of the vegetal pole of the early cleavage stage embryo were injected with Δ1XAR1 RNA. These cells normally give rise to endoderm and never form neural tissues. Surprisingly, injection of Δ1XAR1 in vegetal pole cells leads to the formation of ectopic neural structures in the embryo. Lineage tracing experiments in which a single vegetal pole cell is coinjected with Δ1XAR1 and β-Gal RNAs shows that the fate of the injected vegetal cell is changed when compared to the controls injected with globin and β-Gal RNAs.

Moreover, while injected control cells (e.g. globin injected) populate mostly endodermal tissues, the cells that have received the Δ1XAR1 mostly occupy dorso-anterior positions in the embryo. Whole mount immunohistochemistry of such injected embryo depicts neural tissue that has expanded, and that this expansion correlates with the presence of the lineage tracer (β-Gal). These experiments illustrate that Δ1XAR1 can neuralize embryonic cells in vivo by recruiting cells and changing their original fate, thereby increasing the amount of neural tissue dramatically.

The ability of Δ1XAR1 to induce neural structures in ventralized embryos completely lacking axial structures was also explored. Embryos were UV irradiated during the first cell cycle and co-injected with RNAs encoding Δ1XAR1 and β-Gal in a single blastomere of the early blastula stage. The embryos were then allowed to develop until sibling non UV irradiated embryos reached tailbud stages and were then stained for β-Gal and for the presence of the neural marker NCAM. Comparison of the staining of the neuroaxis of a normal embryo (which is substantially lacking in UV irradiated embryos) with ventralized embryos expressing Δ1XAR1 and β-Gal demonstrating that (i) Δ1XAR1 can induce neural tissue in embryos otherwise lacking dorsal structures, (ii) the neural tissue actually forms a structure that resembles a neural tube, and (iii) the cells that have received the RNA as marked by the lineage tracer are part of the neural tissue. These observations further establish that Δ1XAR1 can neuralize tissues in vivo even in embryos where no axial mesoderm is present.

An other observation made during these experiments was that while the truncated receptor completely and specifically blocked the early morphogenetic response of animal caps exposed to activin, it did not affect the response to bFGF. An unexpected observation is that animal caps derived from Δ1XAR1 injected embryos, including those incubated in buffer alone, formed cement glands. Control and uninjected animal caps did not form cement gland or mesodermal tissues.

Early and late molecular markers for mesoderm induction were also specifically blocked by the truncated activin receptor. In animal caps treated with activin, Xenopus brachyury (Xbra) and Xhox-4, a homeobox protein closely related to Mix-1 (Rosa, F. M. (1989) Cell 57:965–974), were used as immediate early markers for mesoderm induction. When animal caps injected with the Δ1XAR1 RNA were incubated with activin, the expression of both Xbra and Xhox-4 was blocked. The specificity of this block was demonstrated by the fact that induction of Xbra by bFGF was not inhibited. In fact, Xbra induction by bFGF was enhanced in the presence of Δ1XAR1. In midgastrulae, brachyury is normally present as a ring in the lower part of the marginal zone (Smith et al. (1991) Cell 67:79–87) and is a marker for prospective dorsal, lateral, as well as ventral mesoderm. Xhox-4, like Mix-1, marks the early vegetal cells as well as the prospective dorsal and ventral mesoderm. Therefore, the inhibition of Xbra and Xhox-4 expression indicated that all types of mesoderm were blocked by the truncated receptor. Further support for this assertion came from the fact that goosecoid, a marker for head mesoderm at the midgastrula stage, was absent in all injected caps, and the induction of Xwnt-8 expression, a marker for ventral mesoderm, in response to activin, was blocked by injection of the truncated activin receptor. Expression of muscle actin, a mesoderm-specific gene that is expressed at the end of gastrulation and increases during neurulation, was also selectively inhibited in animal caps injected with the truncated receptor. The block to induction of muscle actin was found to be dependent on the dose of Δ1XAR1. It is interesting to note that bFGF induced muscle actin to roughly 10-fold higher levels in caps injected with the truncated activin receptor compared with control caps. This data, and the enhancement of Xbra expression in response to bFGF in the presence of Δ1XAR1, is interpreted to indicate that activin antagonizes the mesoderm-inducing capacity of bFGF and that the mutant receptor, by blocking the effect of activin, amplifies or unmasks additional inducing activities of bFGF. This observation demonstrates a functional redundancy in embryonic cells whereby a block in one signaling pathway can lead to the enhancement of a parallel pathway to compensate for the effect.

The experiments reported here show that disruption of activin signaling can, in the extreme phenotype, prevent mesoderm induction and dorsal body axis formation. Histological differentiation of mesodermal tissue is missing, early and late molecular markers are blocked and gastrulation does not proceed. These results establish activin as a principal determinant of mesoderm induction in vivo and not merely a molecule that mimics some other inducer.

EXAMPLE 2

Endogenous Mesoderm Inducing Signal(s) Inhibited

The experiments illustrated in Example I above demonstrate that a truncated activin receptor can block the induction of mesoderm in explanted animal cap cells. In whole embryos, mesoderm is derived from the marginal zone (the equatorial region of the blastula) rather than from animal cap cells, which normally follow an ectodermal fate. To test whether the truncated receptor can block induction of mesodermal markers in the marginal zone of intact embryos, the truncated receptor was injected into one cell of two-cell embryos. In each case the uninjected half of the embryo served as a control The expression of brachyury, which is expressed as a complete ring in control embryos, was reduced to a half ring in injected embryos. This indicated that the truncated activin receptor blocked the induction of Xbra RNA in cells that form mesoderm in vivo.

The experiments described herein further suggest that it would be possible to determine the phenotype of whole embryos lacking mesoderm and its accompanying morphogenetic movements. Embryos injected with the truncated activin receptor in both cells at the two-cell stage display a range of phenotypes, all of which are markedly deficient in mesodermal and axial development.

TABLE 1

Axial defect produced in embryos injected with Δ1XAR1

| RNA Injected | Δ1XAR | | β-Globin | |
|---|---|---|---|---|
| Phenotype | n | Percent | n | Percent |
| No axial structures | 40 | 53 | 0 | 0 |
| Partial axial defects | 18 | 24 | 2 | 2 |
| Normal embryos | 17 | 23 | 92 | 98 |
| Number of embryos scored | 75 | 100 | 94 | 100 |

Embryos were injected with 4 ng of either Δ1XAR1 or β-globin RNA in the equatorial region of both blastomeres of the two-cell embryo. Embryos were allowed to develop until sibling uninjected controls reached the tail-bud stage, at which time the survivors were scored for their phenotypes. Of the embryos without axial structures, roughly half showed minimal evidence of gastrulation (scant bottle-cell formation only) and had no detectable muscle or notochord either by histology or by molecular marker assay. The others showed only partial gastrulation and contained less than 20% of the normal amount of these markers. Partial axial defects are animals without heads or tail and with less than 50% of the normal amount of notochord and muscle. This division into classes, extreme and partial defects is arbitrary in that a range of defect is observed. n=Number of embryos.

By the time controls reach the tail-bud stage, injected embryos showing the extreme phenotype (about 50% of those injected) were grossly deficient in their development. In the most extreme cases there was no sign of body axis formation, and although the embryos appear to have retained an animal-vegetal axis, there was little indication of an anterior-posterior or dorsal-ventral body plan. Occasionally, some bottle cells formed and gastrulation began, but invagination rarely proceeded beyond a small lip. As observed in injected animal cap explants, cement gland differentiation did occur. Histological sections revealed no evidence of mesodermal differentiation or gastrulation in the extreme cases. The blastocoel remained intact and there was virtually no rearrangement of the presumptive germ layers. Assays for molecular markers of differentiation showed that these embryos did not form notochord, express muscle actin or Xbra RNA. The absence of mesodermal differentiation, as assayed by muscle actin and Xbra RNA expression, was dependent on the dose of truncated activin receptor RNA injected. At 4 ng of injected RNA, muscle actin and brachyury expression were both drastically reduced.

The rest of the embryos showed, to varying degrees, rudimentary signs of mesodermal development, gastrulation and axis formation, but normal embryos were not produced. There was always a marked reduction in notochord and muscle formation, with most of the embryos in this class forming less than half the normal amount of notochord or muscle. None of these mesodermal or axial defects were observed to any significant degree in embryos injected with control RNAs.

EXAMPLE 3

Rescue by Wild-type Activin Receptor

If disruption of activin signaling by the truncated activin receptor is the cause of the mesodermal and axial deficiencies observed, then injection of wild-type activin receptor should rescue the phenotype. Indeed, injecting increasing amounts of wild-type activin receptor RNA with a constant amount of RNA encoding the truncated receptor can rescue embryos, as judged by gross morphology and molecular assays for mesodermal markers. Interestingly, the rescue requires a relatively low amount of wild-type activin receptor and that larger concentrations of the wild-type receptor generate multiple and bent axes, as is observed by ectopic expression of the wild-type receptor alone.

EXAMPLE 4

Neuralization of Embryonic Ectoderm With Δ1XAR1

The studies set out in Examples 1–3 demonstrate that a truncated form of the activin receptor, such as Δ1XAR1, inhibits activin signaling and alters the fate of animal cap cells from epidermal to neural. This neuralization of the cap, assayed by N-CAM expression, was direct in that no cells of mesodermal fate were detected. Further characterization of the neuralizing activity of Δ1XAR1 was performed using animal cap explants.

Xenopus embryos were injected at the 2-cell stage with different concentrations of Δ1XAR1 or control RNA. Animal caps were removed at blastula stages and cultured in saline solution until sibling controls reached the early tailbud stages. RNA was extracted and analyzed by Northern blot techniques for the presence of neural-specific markers. Animal caps injected with Δ1XAR1 expressed two general neural markers: N-CAM, which is exclusively and ubiquitously expressed in the central nervous system (CNS) of Xenopus embryos and a transcript encoding the β-tubulin isotype II, which is also exclusively expressed in the CNS. Injection of globin RNA did not promote expression of these neural markers.

In the preceding examples, it is shown that animal cap cells expressing the truncated activin receptor do not express any mesodermal markers. Immediate early and late as well as dorsal and ventral mesodermal markers were all assayed and found not to be expressed in cells injected with Δ1XAR1 mRNA. In the present experiment, both neural markers, as well as the cement gland (XAG1) marker (Sive et al., (1989) *Cell*, 58:171–180), are expressed in the absence of axial mesoderm as tested by the muscle marker (cardiac actin; Gurdon et al., (1985) *Cell* 41:913–922. The cement gland is an ectodermal tissue located anterior to the forebrain. Thus, neuralization of prospective ectoderm by expression of Δ1XAR1 is neither preceded by, nor dependent upon, mesoderm induction, further confirming that the neural induction is direct.

EXAMPLE 5

The Neural Tissue Induced by Δ1XAR1 is Patterned

During early neurogenesis, the neural plate, although comprised of morphologically indistinguishable cells, displays an anteroposterior and mediolateral polarity. For example, engrailed-2 (En-2), a marker for midbrain-hindbrain structures (Hemmati-Brivanlou and Harland, (1989) *Development* 106:611–617), and Krox-20, a marker of rhombomeres 3 and 5 in the hindbrain (Bradley et al., (1993) *Mech Dev* 40:73–84), are both expressed as stripes with sharp anteroposterior boundaries. Since Δ1XAR1 changes the fate of ectodermal cells from epidermal to neural, whether this neuralized tissue was patterned was tested by using Northern blots, immunohistochemistry, or reverse transcription polymerase chain reaction (RT-PCR) to score for a series of regionally expressed neural markers.

The monoclonal antibody (MAb) 3C3 stains the entire CNS of Xenopus embryos, and MAb 25.4 stains mostly the sensory nervous system. Both MAbs were used to assay animal caps derived from embryos injected with either Δ1XAR1 or globin control mRNA. It was observed that animal caps injected with Δ1XAR1 (7 of 10), but not those injected with globin (0 of 10), stained positively with MAb 3C3. The cells expressing this neural-specific antigen were present in a cluster and not dispersed throughout the explant. Since lineage tracers coinjected with Δ1XAR1 mRNA showed that nearly all cells of the explanted animal caps contain Δ1XAR1 mRNA, these results indicate that only a subset of cells expressing Δ1XAR1 express the CNS antigen recognized by MAb 3C3. It was observed that animal cap cells expressing Δ1XAR1 stain with MAb 25.4 (8 of 10 animal caps), while those expressing globin do not. This suggests that some of the neuralized cells have adopted the fate of the sensory neurons.

Expression of neural markers for different positions along the anteroposterior axis in animal caps was scored using RT-PCR, when sibling controls reached the tailbud stage. Opsin, an eye marker (Saha and Grainger, (1993) *Mol Brain Res* 17:307–318), En-2, Krox-20, and tanabin were assayed. The eye is derived from the forebrain; thus, opsin expression indicates the existence of forebrain cells. Expression of En-2 suggests the presence of midbrain cells. Tanabin is a neural-specific intermediate neurofilament that demarcates rhombomeres 2, 4, 6, and 8 of the hindbrain, the trigeminal ganglia, and a few cells in the eye, forebrain, and spinal cord. The presence of hindbrain cells is less certain, since Krox-20 expression is very weak, and tanabin expression might suggest the presence of more anterior CNS cells, such as photoreceptors or forebrain. All these markers were found to be expressed in caps previously injected with Δ1XAR1, but not in uninjected or globin-injected caps. The spinal cord-specific marker Xlhbox-6 (Wright et al., (1990) *Development* 109:225–234) was absent or expressed at low levels in the Δ1XAR1 explants. The presence of N-CAM and the absence of muscle actin expression in these injected explants demonstrate that these markers are expressed in the absence of mesoderm induction. These results are summarized below in Table 2.

TABLE 2

Neural Markers Scored in Animal Caps Injected with the Dominant Negative Activin Receptor (D1XAR1)

| Marker | Expression |
| --- | --- |
| General Neural Matters | |
| N-CAM | + |
| β-Tubulin Isotype II | + |
| 3C3 | + |
| Anteroposterior Markers | |
| Ospin | + |
| Tanabin | + |
| En-2 | + |
| Krox-20 | + |
| Xlhbox-6 | − |
| Dorsoventral Marker | |
| Tor 25.4 | + |
| Other Ectodermal Marker | |
| XAG1 | + |

For Table 2: markers in all cases have been scored when sibling controls have reached the tailbud stage. NCAM, β-tubulin isotype II, and 3C3 are general neural markers and are all expressed. The anteroposterior markers include opsin, a marker of the photoreceptors of the eye, En-2, which demarcates posterior midbrain and anterior hindbrain Krox-20, which demarcates rhombomeres 3 and 5 of the hindbrain, and tanabin, a marker of rhombomeres 2, 4, 6, and 8, the trigeminal ganglia, and a few cells in the eye and spinal cord. Xlhbox-6 is a marker of the spinal cord. Tor 25.4 is a marker of sensory neurons. XAG1 is cement gland marker. The data presented in this table are a combination of results obtained by Northern blots, RT-PCR, and whole-mount immunohistochemistry.

EXAMPLE 6

Δ1XAR1 Diverts Prospective Ectodermal and Endodermal Blastomeres to a Neural Fate in Whole Embryos The results described above show that inhibition of activin type II receptor signaling leads to neuralization and patterning of presumptive embryonic ectoderm in explants. To confirm that this neuralization could occur in whole embryos, synthetic RNA encoding Δ1XAR1 was injected into prospective ectodermnal cells of wild-type embryos. In the first set of experiments, RNA encoding Δ1XAR1 was injected into the animal pole of the early embryo, the region that gives rise to the future ectoderm, which in turn becomes epidermal or neural. Targeting Δ1XAR1 to the site of prospective ectoderm was found to lead to embryos with grossly exaggerated neural structures. Injected embryos form up to eight eyes and five cement glands. Histological examination revealed that Δ1XAR1-injected embryos display a hypertrophy of the normal CNS as well as ectopic neural tissue. Thus, expression of Δ1XAR1 in the prospective ectoderm amplified the formation of neural tissue.

In a second set of experiments, a single cell at the vegetal pole of 8-cell albino embryos was coinjected with Δ1XAR1 and β-galactosidase (β-gal) RNA (as a lineage tracer). Albinos were used because they are better suited for whole-mount analysis of lineage tracers and molecular markers. Of the four vegetal blastomeres, the two ventral blastomeres contribute primarily to posterior gut and posterior somites (Moody and Kline, (1990) *Anat Embryol* 182:347–362). The dorsal pair contributes primarily to prechordal head mesoderm and pharyngeal endoderm. Neither dorsal nor ventral vegetal cells normally give rise to anterior neural tissue (Moody and Kline, Supra). Since albino embryos were injected, no distinction could be made between prospective dorsal or ventral vegetal blastomeres. The results demonstrated, in confirmation of the observations made above, that the fate of prospective dorsal and ventral vegetal blastomeres is changed to anterior neural tissue as a consequence of Δ1XAR1 expression. The progeny of vegetal blastomeres injected with control globin and β-gal RNA do not contribute to neural tissue (49 of 50). However, coinjection of Δ1XAR1 and β-gal RNA into vegetal cells did result in the relocation of most of the progeny of the injected cells into the dorsoanterior region of the embryo (50 of 50); This relocation of cells is similar to what has been observed in blastomeres expressing the homeobox gene goosecoid (Niehrs et al., (1993) *Cell* 72:491–503). In agreement with the fact that Δ1XAR1 induces anterior neural tissue in animal cap explants, most of these injected cells participate in neural tissue such as forebrain, midbrain, and eyes. In addition, some cells have incorporated into axial mesodermal derivatives such as somites.

In this same injection experiment, double staining with the neural-specific antibody 3C3 confirmed that, in addition to populating the normal CNS, the progeny of injected cells contributed to ectopic neural tissue detected. A dose of Δ1XAR1 mRNA (500 pg per embryo) that did not completely block mesoderm induction in animal cap explants was injected in these experiments. Thus, vegetal cells (prospective endoderm) expressing the truncated activin receptor change their fate to neural, whereas these cells would normally not contribute significantly to anterior neural structures.

EXAMPLE 7

Δ1XAR1 Neuralizes UV-Ventralized Embryos Without Axial Rescue

To investigate further the neuralizing properties of the truncated activin receptor, its effect on embryos ventralized by UV irradiation was determined. Irradiation of the vegetal pole of a fertilized egg during the first cell cycle leads to ventralization, the formation of embryos without the dorsal axial structures, somatic muscle, notochord, or neural tube (Malacinski et al., (1975) *Dev Biol* 56:24–39), Scharf and Gerhart, (1983) *Dev Biol.* 99:75–87). UV-irradiated embryos were coinjected with RNAs encoding either a Δ1XAR1 and β-gal or globin and β-gal as a negative control. A single vegetal blastomere was injected at the 8- to 16-cell stage, the embryos were allowed to develop until sibling non-UV-irradiated controls reached tailbud stages, and the embryos were stained for, β-gal and for the presence of the general neural marker 3C3.

The results demonstrated that Δ1XAR1 can induce neural tissue in embryos that would otherwise lack dorsal structures and that the induced neural tissue forms a tube-like structure resembling a neural tube. The cells that received the Δ1XAR1 RNA, as marked by the expression of β-gal, were part of the neural tissue. However, not all neural cells contain lineage tracer. Some neural cells could be formed secondarily by signals spreading from neural cells injected with Δ1XAR1. The induction of neural structures, even though patterned as a rudimentary tube, does not apparently lead to the complete axial rescue of the ventralized phenotype of the UV embryos. These results further establish that a Δ1XAR1 can neuralize tissues in vivo.

A complicating fact was the observation of some muscle-specific antigen (12/101 staining) in UV embryos injected with Δ1XAR1. The cells stained with 12/101 do not stain for β-gal and are therefore not derived from the injected blastomere. This result raises the interesting possibility that the neural tube could induce or pattern surrounding muscle.

EXAMPLE 8

Cloning of the Xenopus Follistatin

To further address whether activin is the endogenous inhibitor of neural differentiation, the activity of two known specific inhibitors of activin follistatin and inhibin, were assayed. Since no Xenopus full length cDNAs for these two proteins were available, the possible neuralizing activity of the corresponding rat genes were originally tested in vitro by the animal cap assay. Neuralization of Xenopus embryonic tissue was observed with both rat follistatin and inhibin.

The same experiments were also performed with the Xenopus homologs. To perform this experiment, a full length follistatin clone from a Xenopus cDNA library was isolated by standard protocols. The sequence of this clone contains a signal peptide, which is typically indicative of a secreted factor, and three closely related domains, previously reported as "follistatin modules" (Patthy et al. (1993) *Trends in Neurol. Science* 16:76–81), that encompass about 75% of the mature protein. It is noted that follistatin modules have been recently recognized in at least four other proteins such as osteonectin, agrin, a protein SC1 from rat brain, and human testican. While SC1, testican and osteonectin have one follistatin module, agrin has nine tandemly repeated modules at its N-terminus (Patthy et al. (1993) *Trends in Neurol. Science* 16:76–81).

In all species from which the follistatin cDNAs have been isolated, including humans, pigs, rats and Xenopus, two type of transcripts have been detected. Sequence analysis, S1 mapping and RNase protection using the human, porcine and rat genomic clones have revealed that these two transcripts are generated by differential splicing. This differential splicing leads to the translation of two monomeric glycosylated proteins. The smaller molecular weight form in all species studied so far represents a carboxy-truncated form of the larger precursor and is generated by the removal of a highly acidic stretch of acidic amino acids from the larger precursor. The number of amino acids in each protein is used conventionally to name each subtype. Thus the human follistatin proteins are called FS 315 and FS 288; the rat, FS 344 and FS 317; and, the pig, FS 300 and FS 288. Using the same convention, the Xenopus follistatin is termed XFS 319. This protein is the homolog of the smaller subtype of follistatin cloned from other species and lacks the acidic carboxy terminus. Beside the two different lengths of the FS amino acid chains, the native proteins show variations in their degree of glycosylation, which also contributes to the heterogeneity in molecular weight of follistatin (Inouye et al. (1991) *Endocrinology.* 129:815–822).

EXAMPLE 9

Generation of Follistatin Protein, Synthetic RNA and Expression Vectors

A plasmid allowing the production of large amount of active synthetic DNA for follistatin was created. This plasmid pSP64TXFS-319 was generated by subdloning the open reading frame of XFS-319 (SEQ ID No. 1) into the plasmid pSP64T. pSP64T is a derivative of the publicly available pSP64 vector which has been altered to include 5' and 3' untranslated regions of the xenopus β-globin gene to enhance mRNA stability and translation. This construct allows the production of large quantities of capped RNAs that is stable and translationaly enhanced. An epitope tagged version of XFS-319, that is as active as the wild type construct in blocking activin, was generated. This was constructed by adding 12 amino acids originally derived from the human myc protein to the C-terminal end of XFS-319. This molecular tag is recognized by a monoclonal antibody (Ma19E10) and allows the injected follistatin protein to be followed in whole embryos.

Cell culture lines which overexpress a Xenopus follistatin (XFS-319) can be constructed using the pSP64TXFS-319 construct. Following a protocol that has been proven successful in overexpressing human follistatins in Chinese Hamster Ovary cell line (CHO cells) (Inouye et al. (1991) *Endocrinology.* 129:815–822), the open reading frame of XFS-319 can be subcloned into a plasmid containing an SV40 promoter and polyadenylation sequence (pSV2). This vector along with the same vector expressing dhfr (pSV2dhfr) is co-transfected by the calcium phosphate precipitation method into a dhfr-deficient CHO cell line (CHO-DG44). The Xenopus gene is amplified using methotrexate (MTX). Conditioned medium from these transfected cells, along with the untransfected controls, can be used directly, or, where purified protein is required, an activin affinity column can be employed to purify XFS-319 from the conditioned medium as previously described (Inouye et al. (1991) *Endocrinology.* 129:815–822).

Several types of expression vectors can be used for the expression of XFS-319 in embryos. For example, XFS-319 can be placed under the control of the cytoskeletal actin promoter; a powerful, constitutively active promoter. Similarly, XFS-319 can be placed under the control of the Xenopus heat shock promoter. This promoter is only active when the temperature of the recipient embryos, usually kept at 20° C., is raised to 24° C.–25° C. (Harland et al. (1988) *Development* 102:837–852; and Vize et al. in *Xenopus laevis; Practical uses in Cell and Molecular Biology*.ed. Kay and Peng, Academic Press Inc:Florida, 1991). As zygotic transcription in Xenopus does not begin until mid-blastula stages (MBT) such constructs can be useful in determining the later function of follistatin in embryos.

EXAMPLE 10

Expression of Follistatin During Xenopus Development

Northern blot analysis of RNA from different embryonic stages revealed that, as it is the case in mammals, two distinct RNAs of 2.4 and 3.6 kb are transcribed from the follistatin gene, and that the 2.4 kb message is present maternally in the fertilized egg. A partial cDNA clone encoding part of the larger Xenopus follistatin subtype was also isolated recently from Xenopus embryos (Tashiro et al. (1991) *Biochem Biophys Res Comm.* 174:1022–1027). The amino acid identity among species is extremely high, among mammals there is about 98% identity (Inouye et al. (1991) *Endocrinology.* 129:815–822) and between Xenopus and humans there is 86% identity.

The differential splicing leading to the generation of the two protein types does not seem to be under tissue specific regulation since both transcripts are present in all tissues expressing follistatin. The shorter of the human follistatin (HFS 288) has been shown to be 8–10 times more potent in inhibiting activin both in vitro and in vivo (Inouye et al. (1991) *Endocrinology*. 129:815–822). In fact, the shorter form of the human follistatin is the most potent inhibitor of activin, even better than inhibin, the other specific inhibitor of activin (Inouye et al. (1991) *Endocrinology*. 129:815–822). Kinetic analyses of a mixture of human FS binding to activin using a solid phase assay revealed that the FS-activin interaction is of high affinity similar to that estimated for activin binding to its receptor. Inhibin is approximately 500–1000-fold lower in relative potency as compared to activin in the FS binding assay.

EXAMPLE 11

Follistatin is Localized in the Spemann Organizer

Whole mount in situ hybridization (Hemmati-Brivanlou et al. (1990) *Development* 110:325–330) with an anti-sense XFS-319 RNA was used to detect the spatial distribution of follistatin during different stages of Xenopus embryogenesis. The probe used in these experiments is that used on the northern blot and thus can recognize both follistatin transcripts. By this approach, follistatin RNA was first detected at the onset of gastrulation where a few cells of the organizer express XFS transcripts. In the gastrula, follistatin RNA is localized to the dorsal side. The localization is confirmed by RT-PCR on RNAs extracted from dissected embryos at the onset of gastrulation, using the dorsally localized markers noggin (Smith et al. (1992) *Cell* 70:829–840) and Goosecoid (Blumberg et al. (1991) *Science* 253:194–196) as controls.

This region of the embryo has previously been characterized as a potent neural inducer in the animal cap assay. Expressions continues in the anterior two-thirds of the notochord in late gastrula and early neurula stage embryos. Transverse sections of these embryonic stages show that follistatin RNA is expressed in a subset of cells of the prechordal and chordal mesoderm. This expression is strongest in the anterior involuting mesoderm and fades in intensity toward the posterior end. In early neurulae, when the neural plate is still open, the expression of follistatin is confined to head mesoderm and anterior notochord. A traverse section of these early neurula show that, in addition to the expression in the dorsal mesoderm, follistatin RNA can also be detected in a few cells of the hypochord, just ventral to the notochord. At these stages, the portion of the anterior notochord expressing follistatin touches the floor of the diencephalon (forebrain) and underlies the midbrain, hindbrain, and about half of the anterior spinal chord. The expression in the notochord extends posteriorly as development proceeds and includes the entire notochord by stage 21. The organizer region of the embryo has previously been characterized as a potent neural inducer in the animal cap assay. Thus, the temporal and spatial localization of follistatin is in perfect agreement with the site generally predicted to contain the neural inducing activity.

After the neural tube is formed, follistatin RNA is also detected in the forebrain, presumptive midbrain, midbrain-hindbrain junction, and hindbrain. Furthermore, there is a transient follistatin expression in the pronephrous and ventrolateral mesoderm near the blood islands. There is also expression in photoreceptor of the retina at the tailbud stage. At the swimming tadpole stage, most of the expression is localized to the notochord and the head. In the forebrain, the expression of follistatin is confined to three stripes distributed dorsoventrally in the cells of the ventricular zone. There is no apparent staining in the floor or roofplate of the neural tube.

EXAMPLE 12

Xenopus Follistatin RNA and Protein Block Mesoderm Formation and Morphogenetic Movements Induced by Activin The ability of follistatin to inhibit activin activity was tested by two independent approaches. In the first set of experiments, embryos were injected at the 2-cell stage in the animal pole of both blastomeres with 1 ng of either XFS-319 RNA or globin control RNA. The embryos were allowed to develop until they reached blastula stage 8, at which point the animal caps were dissected and incubated in either buffer alone or activin. While injection of control globin RNA apparently had no effect on activin induced morphogenetic movements, injection of XFS-319 completely blocked the morphogenetic movements associated with induction by activin treatment. In addition, animal caps injected with XFS-319 and incubated in buffer or activin were found to show clear cement glands, which parallels the effect of the dominant negative activin receptor described above.

In the second set of experiments, either 50 ng of RNA encoding XFS-319 or 12 ng of RNA encoding Xenopus activin Pb was injected into mature (stage 6) Xenopus oocytes. After 48 hr, medium conditioned by these oocytes or by uninjected oocytes was collected and applied to animal cap explants of stage 8 blastula embryos. It was observed that when the explants were incubated in either buffer alone or conditioned medium from uninjected oocytes, they remained spherical. In contrast, explants incubated in conditioned medium from activin-injected oocytes elongate drastically. Animal caps incubated in medium conditioned by oocytes injected with XFS-319 remained spherical. Finally, when conditioned media from oocytes injected with activin and XFS-319 were mixed at 1:1 ratio, the morphogenetic movement induced by activin is completely blocked. The results of these two experiments demonstrate that XFS-319, like its homologs in other species, is a potent inhibitor of activin.

To assess the potency of this inhibition, a dose response study was carried out in which the animal poles of 2-cell stage embryos were injected with either control globin RNA or different concentrations of XFS-319. As in the first set of experiments, animal caps from injected embryos were explanted at stage 8 and incubated with the potent mesoderm inducer activin. These caps were cultured until sibling uninjected embryos reached tailbud stage, at which point total RNA was isolated from the explants and analyzed by Northern blotting. While 4 ng of the control globin RNA did not seem to interfere with the mesoderm inducing activity of activin, as assayed by the expression of the axial mesodermal marker muscle actin, 250 pg of XFS-319 RNA was found to be enough to block activin action completely. In addition, none of the animal caps injected with 4.00, 1.00, or 0.25 ng of XFS-319 RNA and treated with activin (20 explants for each concentration) showed any sign of elongation.

EXAMPLE 13

Follistatin is a Direct Neural Inducer

We tested for direct neural inducing activity of XFS-319 was also tested in animal cap explants. An indication that XFS-319 might possess this type of activity came from the observation that cement glands were induced in explants injected with XFS-319. Embryos were injected at the 2-cell stage in the animal pole with 2 ng of XFS-319 RNA, and it was found that the injection of this RNA elicits induction of neural tissue in the animal cap, as demonstrated by the expression of the general neural markers N-CAM and β-tubulin isotype II. These markers were expressed in the absence of muscle actin, suggesting that this induction is direct, i.e., without concomitant mesoderm induction. It is further noted that this represents the first evidence of a single endogenous embryonic molecule with neural inducing follistatin also provides evidence for activin as the inhibitor of neuralization.

Induction of the general neural marker in these explants clearly demonstrates the neuralizing activity of XFS-319. However, although this induction happens in the absence of the muscle actin marker, other mesodermal tissues could still be present. To address this question, XFS-319 or a control RNA was injected under the same conditions as described above. A portion of the animal cap explants were processed when sibling controls reached midgastrula stage to analyze the expression of immediate early mesodermal markers, and the rest were allowed to develop until tailbud stage and then assayed for muscle actin and neural markers. Uninjected animal caps, or explants injected with either XFS-319 or control RNA incubated in buffer alone, failed to express any of the five mesodermal markers assayed. The early dorsal-specific mesodermal markers goosecoid and noggin, as well as the ventral marker Xwnt-8(Christian et al. (1991) Development 111:1045–1056 and the general early mesodermal markers X-bra (Smith et al., (1991) Cell 67:79–87) and Mix-1 are not expressed in caps that were injected with 2 ng of XFS-319 RNA. Uninjected animal caps, in contrast, did express all of these markers in response to activin. In addition, the explants that were left to develop until tailbud stage also were found to express the neural marker N-CAM, but not muscle actin, demonstrating that XFS-319 was active in inducing neural tissue in these experiments. These experiments further support the notion that the neuralizing activity of XFS-319 happens in the absence of scorable mesoderm and is, by this definition, direct. In addition, the fact that follistatin does not induce noggin expression suggests that either the mechanism of neural induction by follistatin is independent of noggin action or that follistatin acts downstream of noggin in this regard.

EXAMPLE 14

Dose of Follistatin RNA Required for Neural Induction

We next aimed to characterize the direct neural inducing activity of follistatin by measuring the doses required for induction of a general neural marker and cement glands in animal cap explants. Embryos were injected at the 2-cell stage in the animal pole with different concentrations of XFS-319 RNA. Animal caps from injected embryos were explanted at the blastula stage and allowed to develop until sibling uninjected controls reached the early tailbud stage. RNA extracted from explants injected with different concentrations of XFS-319 along with RNA from uninjected explants and control embryos were analyzed by Northern blots. It was also observed that the general neural marker β-tubulin isotype II can be induced in these caps by injection of as little as 50 pg of XFS-319 RNA, while the cement gland markerXAG-1 (Sive et al., (1989) Cell 58:171–180) requires a minimum of 250 pg. The muscle actin panel again demonstrated that neuralization was direct and that the explants did not contain mesoderm.

EXAMPLE 15

Follistatin Induces Anterior Neural Markers

Examples 1–7 above demonstrate that interference with signaling through the type II activin receptor in embryonic explants results in the induction of anterior neural markers. Since follistatin interferes with activin signaling by a different mechanism, it is important to ask what type of neural tissue is induced by XFS-319 expression in animal cap explants. To this end, the same experiment described in Example 13 was performed, and RT-PCR was used to score for the range of anteroposterior neural markers. As was the case for the truncated activin receptor, the anterior neural markers opsin, which demarcates the photoreceptors of the retina derived from the forebrain, En-2, a marker of the midbrain-hindbrain junction, and tanabin, principally a marker of hindbrain, trigeminal ganglia, and a few cells of the eye, forebrain, and spinal cord were all induced by follistatin. Interestingly, Krox-20, another hindbrain marker, and Xlhbox-6, the spinal cord marker, are not detected in these caps. These results are summarized in Table 3.

TABLE 3

| Neural Markers Scored in Animal Caps Injected with XFS-319 RNA | |
|---|---|
| Marker | Expression |
| General Neural Matters | |
| N-CAM | + |
| β-Tubulin Isotype II | + |
| Anteroposterior Markers | |
| Opsin | + |
| Tanabin | + |
| En-2 | + |
| Krox-20 | − |
| Xlhbox-6 | − |
| Dorsoventral Marker | |
| Other Ectodermal Marker | |
| XAG1 | + |

For Table 3: markers in all cases have been scored when sibling controls have reached the tailbud stage. N-CAM and β-tubulin isotype II are general neural markers and are both expressed. The anteroposterior markers include opsin, which is a marker of the photoreceptors of the eye, En-2, which demarcates posterior midbrain and anterior hindbrain, Krox-20, which demarcates rhombomeres 3 and 5 of the hindbrain, and tanabin, a marker of a few cells of the forebrain and retina but mostly rhombomeres 2, 4, 6, and 8 and the trigeminal ganglia. Xlhbox-6 is a marker of the spinal cord. XAG1 is a cement gland marker. The data presented in this table are a combination of results obtained by Northern blot and RT-PCR.

From these results, we conclude that anterior neural tissue such as forebrain and midbrain is present in animal caps expressing XFS-319. The presence of hindbrain, however, is not well established by this type of assay. The absence of Krox-20 expression suggests that rhombomeres 3 and 5 are not present in these explants. Tanabin expression can be interpreted either as the presence of even-numbered rhombomeres or simply as confirmation of the presence of midbrain or forebrain. The absence of Xlhbox-6 signal suggests that posterior neural tissue such as spinal cord is absent. The staining patterns for N-CAM and muscle actin confirmed that this neuralization is direct.

EXAMPLE 16

Activin, but not Noggin, Induces the Expression of Follistatin

The protein noggin has been previously demonstrated to induce neural tissue in animal cap explants (Lamb et al., (1993) Science 262:713–718). However, while neural induction by noggin is direct, activin, in contrast, is not apparently a direct neural inducer, and the neural tissue in explants treated with activin likely results from a secondary induction by mesoderm. It has been previously shown (Thomsen and Melton, (1993) Cell 74:433–441)), and we have confirmed, that activin can induce the expression of noggin in animal cap explants (see Example 13). Thus, it could be argued that the indirect neural inducing activity of activin is mediated by noggin. Follistatin displays direct neural inducing activity in explants; however, Example 13 demonstrates that this neural induction is not mediated by noggin. To investigate further a possible relationship among the neural inducing activity of noggin, follistatin, and activin, we decided to test the following: first, whether the neural inducing activity of noggin resulted in follistatin expression, and second, whether the neural induction in explants and embryos, in response to activin, could be correlated with follistatin expression.

Embryos at the 2-cell stage were injected with 1 ng of noggin RNA in the animal pole. At blastula stage (stage 8), the animal poles of these embryos along with those of the control injected and uninjected embryos were explanted. Half of the explants were allowed to develop until midgastrula stage (stage 10.5), when neural induction has begun, and then were assayed by RT-PCR for follistatin expression. The other half were allowed to develop until early tailbud stage to provide a positive control for the function of noggin. Under this experimental condition, the expression of noggin in animal cap explants was not observed to induce follistatin. Thus, the neural inducing activity of noggin in animal cap explants is not mediated, at least at the transcriptional level, by follistatin. Noggin in these experiments has apparently been active in inducing the neural marker N-CAM directly in the explants.

To determine if addition of activin to animal cap explants induces the expression of follistatin,? uninjected animal caps dissected at stage 8 were incubated in buffer alone or in the presence of activin. We found that addition of activin to animal caps induces the expression of XFS-319 RNA. Since activin can also induce the expression of noggin in these explants, we conclude that the neural inducing activity of activin may be mediated through either noggin or follistatin, or both.

EXAMPLE 17

Follistatin Expression in Secondary Axes Induced by Activin

When injected into the ventral side of the embryo, activin RNA can also induce a partial secondary axis that includes spinal cord and hindbrain, but not more anterior structures (Thomsen et al., (1990) Cell 63:485–493). Lineage-tracing experiments have shown that the cells that have received activin RNA do not participate in the induced ectopic neural tissue. Thus, we were prompted to ask whether follistatin could be involved in the induction of the ectopic neuraxis. Xenopus activin $\beta_b$ RNA or control RNA was injected into a single blastomere on the ventral side of embryos at the 8- to 16-cell stage. Embryos injected with Xenopus activin $\beta_b$ transcript, but not control RNA, displayed a partial secondary dorsal axis, as previously reported. These embryos were analyzed at neurula stages (stage 21) for the expression and distribution of follistatin RNA by whole-mount in situ hybridization. It was noted that while follistatin RNA is present in the single notochord of the control, most embryos with double axes show the presence of follistatin in both the primary and the secondary axis (n=18 of 25). Thus, the presence of follistatin in the secondary axis may account for the induction of the secondary neuraxis. These experiments demonstrate that activin can induce the expression of follistatin both in embryonic explants and in the context of the whole embryo. Thus, the neural inducing activity of activin may be mediated by either noggin or follistatin, or both.

EXAMPLE 18

Ectopic Injection of Follistatin in Wild Type Embryos

There is a direct correlation between the competence of the ectodermal cells to respond to a neural inductive stimulus and the size of the neural plate. To assay follistatin's effect on the competence of the ectoderm, follistatin RNA can be injected in the animal pole of either one or both cells of a two cell stage embryo. For example, experimental embryos can be coinjected with different concentrations of myc-tagged follistatin and a single concentration of β-Gal. Control embryos will be injected with β-Gal alone. The embryos are allowed to develop until they reach the mid-neurula stage when the neural plate is still open, and then stained as wholemounts for β-Gal and NCAM simultaneously. Since the animal pole of the embryo contributes mostly to epidermal and neural derivatives, the control embryos are expected to display normal size neural plates with β-Gal staining in both the neuroectoderm and the epidermis. Several possible outcomes exist for the experimental embryos. In one scenario, no changes will be detected in the size of the neural plate regardless of the β-Gal distribution, indicating that follistatin did not modify the competence of the animal cap. In another scenario, the embryos still have an expanded neural plate and ectopic neural tissue, with most of the β-Gal and myc positive cells localized within the expanded neural tissue. This latter result would imply that follistatin is capable of changing the competence of the ectodermal cells for neural induction and has led to recruitment of epidermal-fated cells to adopt a neural fate.

The ability of follistatin to induce neural structures on the ventral side can also be tested in similar fashion in the context of the whole embryo. To this end, follistatin and β-Gal RNA, or β-Gal RNA alone, is injected in the ventral side of an 8 cell stage embryo. Control and experimental embryos are harvested when sibling controls reach the tailbud stage, and examined by morphology, histology and wholemount staining. Staining for NCAM can also be used to detect any ectopic neural tissue. The formation of a secondary neuroaxis or neural tissue would clearly indicate that follistatin can neuralize in vivo. The β-Gal staining would again be informative as to the fate of the cells making the follistatin protein. In Spemann's original experiment, most of the neural tissue in the secondary axis was derived from the ventral side of the host embryo and did not originate from the organizer. If, β-Gal expressing cells do not participate in the induced ectopic neuroaxis, then experiment have demonstrated that follistatin neural inducing ability parallels the neural inducer of the organizer. If no ectopic neural tissue is generated, then it might be concluded that other factors from the organizer are also required for the ectopic neural induction. Finally if all cells in the secondary neuroaxis have β-Gal, it would be consistent with a conclusion that even though follistatin can neuralize, this neuralization is not the same as the pathway used by the embryo.

EXAMPLE 19

Injection of Follistatin in UV Embryo

A more stringent assay of the neuralizing activity of follistatin in vivo is to test the ability of this factor to induce a neuroaxis in embryos completely lacking dorsal structures. UV irradiation of the Xenopus embryo during the first cell-cycle leads to embryos lacking a dorsal axis. These embryos have previously been used in an assay system to isolate factors involved in induction and patterning of the axial mesoderm (Smith et al. (1992) *Cell* 70:829–840). In addition most growth factors with organizer activity can rescue a complete or partial dorsal axis in these ventralized embryo. In one embodiment of an assay for other neuralizing activities, β-Gal and different concentrations of follistatin RNA are co-injected into a single blastomere of UV irradiated embryos. The embryos are then allowed to develop until early tailbud stages at which point they are examined by histology and stained as whole mount for β-Gal and NCAM protein. The control embryos can comprise β-Gal injected alone and uninjected embryos. The two latter controls allow assessment of the quality of UV ventralization. A given concentration of follistatin either will or will not induce an ectopic neural tissue. If it does, the level of β-Gal positive cells populating the induced neuroaxis can be determined. The character of the mesoderm surrounding the neural tissue can also be assessed to see if it maintains its ventral nature or whether it has been dorsalized. If the mesoderm is still ventral in nature, in might be concluded that follistatin has recruited ventral ectodermal cells for the formation of the ectopic neural tissue. If the mesoderm has been dorsalized (i.e. if markers of dorsal mesoderm such as muscle actin or notochord are present) then whether the mesodermal or the neural tissue was induced first will need to be determined.

All of the above-cited references and publications are hereby incorporated by reference.

Equivalents

Those skilled in the art will recognize, or be able to ascertain using no more than routine experimentation, numerous equivalents to the specific methods and reagents described herein. Such equivalents are considered to be within the scope of this invention and are covered by the following claims.

What is claimed is:

1. A method for inducing a stem cell having activin receptors responsive to activin to differentiate to a neuronal cell phenotype, which stem cell is provided in a culture of two or more cells in vitro, comprising providing said cell with a first agent that antagonizes the biological action of activin selected from follistatin, proteins that include at least one follistatin module, an α2-macroglobulin, and an inhibin, and a second agent which agent is a neurotrophic factor that enhances a particular differentiation fate of the cell, wherein said first agent and second agent are provided in amounts sufficient to induce differentiation of said cell to a neuronal cell phenotype.

2. The method of claim 1, wherein said first agent inhibits the biological activity of activin by preventing activin from binding activin receptors on the surface of said cell.

3. The method of claim 2, wherein said antagonizing agent binds activin and sequesters activin such that it cannot bind said activin receptors.

4. The method of claim 3, wherein said antagonizing agent is selected from follistatin, an α2-macroglobulin, and a protein containing at least one follistatin module.

5. The method of claim 2, wherein said antagonizing agent inhibits binding of activin with said activin receptors via its own binding to said activin receptor.

6. The method of claim 5, wherein said antagonizing agent is an inhibin.

7. A method of claim 1, wherein said neuronal cell phenotype comprises a neural progenitor cell.

8. The method of claim 7, wherein said neural progenitor cell is selected from a melanocyte progenitor cell, a glial progenitor cell, a sensory neuron progenitor cell, a sympatho-adrenal progenitor cell, a parasympathetic progenitor cell, and an enteric progenitor cell.

9. The method of claim 1, wherein said stem cell is selected from an embryonic cell, a fetal cell, and a neonatal cell.

10. The method of claim 1, wherein said neuronal cell phenotype is a glial cell.

11. The method of claim 1, wherein said neuronal cell phenotype is a nerve cell.

12. The method of claim 1, wherein said cell is further contacted with an antimitotic agent in an amount sufficient to reduce the rate of growth of glial cells and favor the growth of nerve cells.

13. The method of claim 1, wherein the second agent is selected from ciliary neurotrophic growth factor, schwannoma-derived growth factor, glial growth factor, striatal-derived neuronotrophic factor, platelet-derived growth factor, scatter factor, a vertebrate hedgehog protein, noggin, and a ligand for a Notch receptor.

14. A method for enhancing survival of at least one neuronal cell having activin receptors responsive to activin, which neuronal cell is provided in a culture of two or more cells in vitro, comprising contacting said cell with an agent, selected from follistatin, proteins that include at least one follistatin module, an $\alpha$2-macroglobulin, and inhibin, that antagonizes the biological action of activin, in an amount sufficient to enhance survival of said cell.

15. The method of claim 14, wherein said cell is further contacted with a second agent which agent is a neurotrophic factor which enhances a particular differentiation fate of the cell.

16. The method of claim 15, wherein the second agent is selected from ciliary neurotrophic growth factor, schwannoma-derived growth factor, glial growth factor, striatal-derived neuronotrophic factor, platelet-derived growth factor, scatter factor, a vertebrate hedgehog protein, noggin, and a ligand for a Notch receptor.

17. The method of claim 14, wherein said cell is a stem cell.

18. A method for inducing at least one progenitor cell to differentiate to a neuronal cell phenotype, which progenitor cell is provided in a culture of two or more cells in vitro, comprising contacting said cell with an agent which disrupts an activin signaling pathway in said cell, wherein said activin signaling pathway normally induces said cell to differentiate to a non-neuronal cell type, said agent is selected from a soluble growth factor-binding domain of an activin receptor, follistatin, proteins that include at least one follistatin module, an $\alpha$2-macroglobulin, and inhibin, and said agent is provided in an amount sufficient to induce differentiation of said cell to a neuronal cell phenotype.

19. A method for inducing at least one cell having activin receptors responsive to activin to differentiate to a neuronal cell phenotype, which neuronal cell is provided in a culture of two or more cells in vitro, comprising contacting said cell with an agent that antagonizes the biological action of activin, selected from follistatin, proteins that include at least one follistatin module, an $\alpha$2-macroglobulin, and inhibin, in an amount sufficient to induce neuronal differentiation, wherein said neuronal cell phenotype is selected from a melanocyte progenitor cell, a glial progenitor cell, a sensory neuron progenitor cell, a sympatho-adrenal progenitor cell, a parasympathetic progenitor cell, and an enteric progenitor cell.

20. The method of claim 19, wherein said cell is further contacted with a second agent which agent is a growth factor having neurotrophic or neural inductive activity.

21. The method of claim 19, wherein said cell is a stem cell.

* * * * *

UNITED STATES PATENT AND TRADEMARK OFFICE
CERTIFICATE OF CORRECTION

PATENT NO.   : 6,686,198 B1
DATED        : February 3, 2004
INVENTOR(S)  : Douglas Melton et al.

It is certified that error appears in the above-identified patent and that said Letters Patent is hereby corrected as shown below:

Column 38,
Lines 56 and 59, after "said" insert -- first -- and delete "antagonizing".

Signed and Sealed this

Nineteenth Day of October, 2004

JON W. DUDAS
*Director of the United States Patent and Trademark Office*